(12) United States Patent
Goodwin et al.

(10) Patent No.: US 7,526,953 B2
(45) Date of Patent: May 5, 2009

(54) METHODS AND APPARATUS FOR THE DOWNHOLE CHARACTERIZATION OF FORMATION FLUIDS

(75) Inventors: Anthony R. H. Goodwin, Sugar Land, TX (US); Pete Hegeman, Stafford, TX (US); Kai Hsu, Sugar Land, TX (US); Chengli Dong, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 266 days.

(21) Appl. No.: 11/615,381

(22) Filed: Dec. 22, 2006

(65) Prior Publication Data
US 2007/0119244 A1 May 31, 2007

Related U.S. Application Data

(60) Continuation-in-part of application No. 11/388,274, filed on Mar. 24, 2006, which is a division of application No. 10/309,849, filed on Dec. 3, 2002, now Pat. No. 7,081,615.

(51) Int. Cl.
*E21B 49/08* (2006.01)
(52) U.S. Cl. .................. 73/152.28; 250/255
(58) Field of Classification Search ............. 73/152.28; 250/255
See application file for complete search history.

(56) References Cited

U.S. PATENT DOCUMENTS

| | | | |
|---|---|---|---|
| 3,859,851 A | 1/1975 | Urbanosky |
| 4,994,671 A | 2/1991 | Safinya et al. |
| 5,167,149 A | 12/1992 | Mullins et al. |
| 5,201,220 A | 4/1993 | Mullins et al. |
| 5,266,800 A | 11/1993 | Mullins |
| 5,331,156 A | 7/1994 | Hines et al. |
| 5,622,223 A | 4/1997 | Vasquez |
| 5,780,850 A | 7/1998 | DeLaune et al. |
| 5,859,430 A | 1/1999 | Mullins et al. |
| 5,939,717 A | 8/1999 | Mullins |

(Continued)

FOREIGN PATENT DOCUMENTS

| | | |
|---|---|---|
| GB | 2304906 | 3/1997 |
| GB | 2345137 | 6/2000 |
| GB | 2391940 | 2/2004 |
| GB | 2410550 | 8/2005 |
| WO | 98/45575 | 10/1998 |

OTHER PUBLICATIONS

Craft, B.C. et al., "Applied Petroleum Reservoir Engineering," Prentice Hall, pp. 59-67, 1959.

(Continued)

*Primary Examiner*—Hezron Williams
*Assistant Examiner*—Rodney T Frank
(74) *Attorney, Agent, or Firm*—Dave R. Hofman; Darla Fonseca; Jaime Castano

(57) ABSTRACT

Methods and apparatus for investigating a hydrocarbon bearing geological formation traversed by a borehole are disclosed. An example method to characterize a fluid associated with an underground geological formation obtains a sample of the fluid associated with the underground geological formation. The example method measures, in a borehole associated with the underground geological formation, a chemical composition and a thermophysical property of the sample of the fluid. The example method selects a mathematical model to represent the sample of the fluid based on at least one of the chemical composition or the thermophysical property and adjusts a parameter of the mathematical model based on at least one of the chemical composition or the thermophysical property to generate an adjusted mathematical model. The example method then determines a property of the fluid associated with the underground geological formation based on the adjusted mathematical model.

20 Claims, 17 Drawing Sheets

U.S. PATENT DOCUMENTS

| | | | |
|---|---|---|---|
| 6,274,865 | B1 | 8/2001 | Schroer et al. |
| 6,350,986 | B1 | 2/2002 | Mullins et al. |
| 6,465,775 | B2 | 10/2002 | Mullins et al. |
| 6,627,873 | B2 | 9/2003 | Tchakarov et al. |
| 6,683,681 | B2 | 1/2004 | DiFoggio et al. |
| 7,002,142 | B2 | 2/2006 | Mullins et al. |
| 7,081,615 | B2 | 7/2006 | Betancourt et al. |
| 7,134,500 | B2 | 11/2006 | Ramakrishnan et al. |
| 2002/0043620 | A1 | 4/2002 | Tchakarov et al. |

OTHER PUBLICATIONS

Ely, J.F. et al., "Prediction of Transport Properties. I. Viscosity of Fluids and Mixtures," I & EC Fund., vol. 20, No. 4, pp. 323-332, 1981.

Lake, L.W., "Enhanced Oil Recovery," Prentice Hall, Chap. 4, pp. 93-104, 1999.

Michelsen, J.L., Calculation of Phase Envelopes and Critical Points for Multicomponent Mixtures: Fluid Phase Equilibria, vol. 4, pp. 1-10, 1980.

Pedersen, K.S. et al., "Properties of Oils and Natural Gases," Gulf Publishing Co., Chapter 5, pp. 79-88, Chapter 11, pp. 172-175, 1989.

Firoozabadi, Abbas, Thermodynamics of Hydrocarbon Reservoirs, Chapter 3, Equation-of-State Representation of Reservoir-Fluids Phase Behavior and Properties, McGraw-Hill Companies, Inc., 1999, pp. 129-153.

McCain, Jr., William D., The Properties of Petroleum Fluids, Chapter 5, The Five Reservoir Fluids, Penwell Publishing, 1990, pp. 147-159.

Schlumberger PVTi Reference Manual 2002A, Chapter 7, Technical Description, Schlumberger Information Solutions, Jul. 2002, pp. 7-1 to 7-17, pp. 7-26 to 7-43, and pp. 7-46 to 7-54.

Danesh, A., "A PVT and Phase Behavior of Petroleum Reservoir Fluids," Developments in Petroleum Science, vol. 47, Elsevier, Amsterdam, 1998.

Wagner, W., Cryogenics, 1972, 12, pp. 214-221.

Halpin, T.P.J. et al., A New Method of Continuous Thermodynamics Applied in an Equation of State, SPE Reservoir Engineering, Nov. 1990, pp. 617-622.

METHODS AND APPARATUS FOR THE DOWNHOLE CHARACTERIZATION OF FORMATION FLUIDS

RELATED APPLICATIONS

This application is a continuation-in-part of U.S. application Ser. No. 11/388,274, filed on Mar. 24, 2006, which is a divisional of U.S. application Ser. No. 10/309,849, filed on Dec. 3, 2002, now issued as U.S. Pat. No. 7,081,615, the disclosures of which are incorporated by reference herein in their entireties.

This application is also related to co-owned U.S. Pat. No. 6,465,775, to G. Fujisawa, et al. entitled "Method for Chemical Composition Analysis in a Downhole Environment," and to co-owned U.S. Pat. No. 5,859,430 to O. Mullins et al., entitled "Method and Apparatus for the Downhole Compositional Analysis of Formation Gases," both of which are incorporated by reference herein in their entireties.

FIELD OF THE DISCLOSURE

The present disclosure relates generally to methods and apparatus for making in situ determinations regarding hydrocarbon bearing geological formations and, more particularly, to methods and apparatus to perform the downhole characterization of formation fluids.

BACKGROUND

Characterizing commercially viable accumulations of hydrocarbons is the main objective of well logging. Downhole sampling and testing tools such as the Modular Dynamic Formation Tester (MDT) (MDT is a trademark of Schlumberger Ltd.) are used during the logging phase to gain a more direct assessment of the production characteristics of the accumulation. The objective of the MDT tool is to provide a controlled channel of hydraulic communication between the reservoir fluid and the wellbore. The tool allows withdrawal of small amounts of formation fluid through a probe that contacts the reservoir rock (formation). In addition to obtaining a more direct measurement of the flow characteristics of the reservoir and the formation pressure, high quality samples of fluid can be obtained for analysis. Historically, the fluid samples were brought to the surface for analysis in a laboratory, but recent developments in the MDT tool have made possible the direct measurement of fluid properties downhole during the pump-out or sampling sequence. Details of the MDT tool and the Optical Fluid Analyzer (OFA) module of the MDT tool may be obtained with reference to commonly owned U.S. Pat. No. 3,859,851 to Urbanosky, U.S. Pat. No. 4,994,671 to Safinya et al., U.S. Pat. No. 5,167,149 to Mullins et al., U.S. Pat. No. 5,201,220 to Mullins et al., U.S. Pat. No. 5,266,800 to Mullins et al., and 5,331,156 to Hines et al., all of which are hereby incorporated by reference in their entireties herein.

The main advantage of downhole analysis is that the fluid is relatively pristine. If the sampling pressure is above the saturation pressure, the fluid will be in a single phase ensuring that the original composition is being analyzed. For pressures below the saturation pressure, a measurement of the properties of the liquid phase in the oil zone and the associated gas above it will yield a more accurate sampling than a sample recombined at the surface. Indeed, it may be difficult to retain the sample in the state in which it existed downhole when it is retrieved to the surface.

Petroleum oil and gas are essentially a mixture of several hydrocarbon components, the variation of which dictates the characteristics of the fluid along with some inorganic substances. Different types of reservoir fluids include black oils, volatile oils, retrograde condensates, wet gases, and dry gases, and the different fluid types require different considerations for their exploitation, and different properties are used for their description. For example, it is generally agreed that black oils and dry gases can be described satisfactorily using averaged properties of the oil and gas phases, such as the volumetric factors and gas solubility ratios. Volatile oils and retrograde condensates, which are near critical fluids, as well as wet gases all require a more detailed knowledge of the fluid composition because the ultimate recovery will be dictated by the control of the production conditions (e.g., primarily pressure).

A downhole fluid analysis provides information in real time in contrast to a laboratory analysis that may last for several days, or surface wellsite analysis, which may result in undesirable phase transitions as well as the loss of key constituents.

A detailed description of the fluid properties is desirable for an accurate modeling of the fluids in the reservoir. Indeed, decisions such as the type of well completion, production procedures and the design of the surface handling and processing facilities are affected by the characteristics of the produced fluids. For example, if fluid in the reservoir is a retrograde condensate, the saturation (dew) pressure, combined with the formation pressure and permeability will dictate the maximum pressure drawdown for production of the fluids, or whether an injection scheme for pressure maintenance or liquid vaporization should be implemented.

SUMMARY

In one described example, a method to characterize a fluid associated with an underground geological formation obtains a sample of the fluid associated with the underground geological formation and measures, in a borehole associated with the underground geological formation, a chemical composition and a thermophysical property of the sample of the fluid. The example method selects a mathematical model to represent the sample of the fluid based on at least one of the chemical composition or the thermophysical property and adjusts a parameter of the mathematical model based on at least one of the chemical composition or the thermophysical property to generate an adjusted mathematical model. The example method may then determine a property of the fluid associated with the underground geological formation based on the adjusted mathematical model.

In another described example, a system to characterize a fluid associated with an underground geological formation includes a device to obtain a sample of the fluid associated with the underground geological formation. The system also includes a first sensor to measure a chemical composition of the sample of the fluid and a second sensor to measure a thermophysical property of the sample of the fluid. Additionally, the example system includes an electronics unit to select a mathematical model to represent the sample of the fluid based on at least one of the chemical composition or the thermophysical property. The electronics unit may also adjust a parameter of the mathematical model based on at least one of the chemical composition or the thermophysical property to generate an adjusted mathematical model. Additionally, the electronics unit may determine a property of the fluid associated with the underground geological formation based on the adjusted mathematical model.

DETAILED DESCRIPTION

Figure 1:
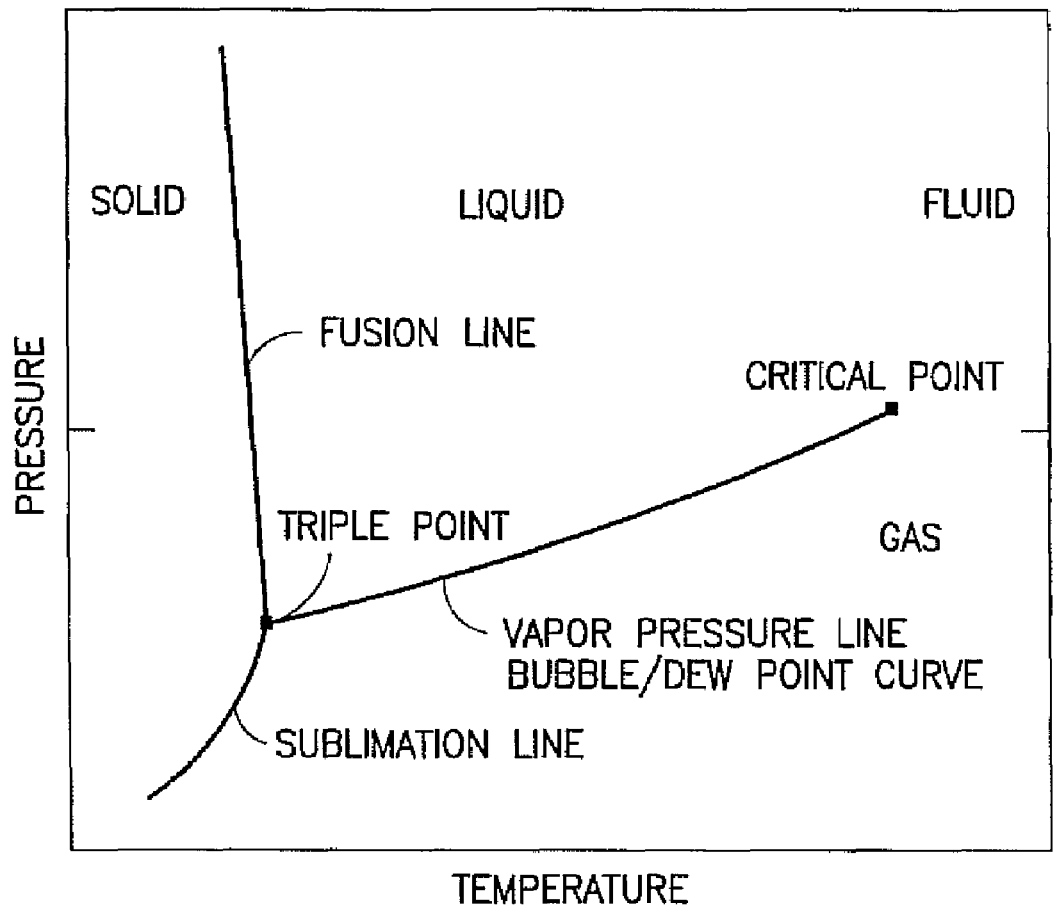
FIG. 1 is a pressure-temperature diagram for a pure component.

As described in greater detail below, in situ determinations regarding hydrocarbon bearing geological formations are made via the use of a sampling tool such as the Schlumberger Modular Dynamic Formation Tester (MDT). Downhole data acquired with the sampling tool are used to conduct a compositional analysis of the reservoir fluid and the compositional analysis of the reservoir fluid is related to a model of the thermodynamic behavior of the fluid; i.e., the mass fractions of the fluid components are used as inputs to an equation of state (EOS) to predict the phase behavior of the fluid. With the reservoir fluid characterized with respect to its thermodynamic behavior, fluid production parameters, transport properties, and commercially useful indicators of the reservoir are computed. For example, the thermodynamic model can provide the phase envelope that can be used to interactively vary the rate at which samples are collected in order to avoid entering the two-phase region. Other properties that may also be useful in assessing the methods required to produce the particular reserve can be estimated from the chosen equation of state. As examples, the density, viscosity, and volume of gas formed from a liquid after expansion to a specified temperature and pressure may be obtained directly from the EOS provided with the chemical composition.

The characterization of the fluid sample with respect to its thermodynamic model can also be used as a benchmark to determine the validity of the obtained sample, whether to retain the sample, and/or whether to obtain another sample at the location of interest. More particularly, based on the thermodynamic model and information regarding formation pressures, sampling pressures, and formation temperatures, if it is determined that the fluid sample was obtained near or below the bubble line of the sample, a decision may be made to jettison the sample and/or to obtain sample at a slower rate (i.e., a smaller pressure drop) so that gas will not evolve out of the sample. Alternatively, because knowledge of the exact dew point of a retrograde gas condensate in a formation is desirable, a decision may be made, when conditions allow, to vary the pressure drawdown in an attempt to observe the liquid condensation and thus establish the actual saturation pressure.

To generate a relatively accurate thermodynamic model of the reservoir fluid it is desirable to obtain an accurate determination of the reservoir fluid composition. Thus, as described in greater detail below, the reservoir fluid composition may be estimated using the Condensate and Gas Analyzer (CGA) module of the MDT tool. More specifically, the CGA module measures absorption spectra and translates them into concentrations of several molecular groups in the fluids of interest. In particular, determinations of the concentrations of methane ($CH_4$), a group containing ethane, propane, butane, and pentane fractions ($C_2H_6$, $C_3H_8$, i-$C_4H_{10}$, n-$C_4H_{10}$, i-$C_5H_{12}$, n-$C_5H_{12}$), a lump of hexane and heavier components ($C_6H_{14}+$), and carbon dioxide ($CO_2$) can be determined. However, the example methods and apparatus described herein may be more generally applied to any desired partitioning of the fluid composition. Thus, if desired, each component of the fluid may be considered separately to potentially increase precision of the modeling.

Before continuing with a more detailed description of the example methods and apparatus, a brief overview of the phase behavior of complex fluids is now provided. Matter can exist in three basic phases, namely: gas, liquid and solid. The phase behavior of a substance refers to all possible states or phases in which the substance is present under certain conditions of pressure and temperature. A "substance" is formed by one or more identifiable "components" or "chemical entities." The term "system" is also to be used in this context as a synonym of "substance".

As is well known, Gibbs phase rule states that the degrees of freedom of a system (NF) is equal to the number of components (NC) minus the number of phases (NP) plus 2, assuming that there are no chemical reactions among components. The number 2 refers to the intensive properties pressure and temperature. The degrees of freedom of a system establish the number of independent intensive properties that must be specified to obtain the thermodynamic state of all the properties of the system.

FIG. 1 depicts a pressure-temperature (P-T) diagram for a pure component (NC=1). When two phases coexist NF equals 1 and the two phases are present along any of the lines depicted in FIG. 1. For three phases NF=0, the phases can only exist under a certain pressure and temperature specified by the triple point. A critical point exists at the end of the gas/liquid phase boundary line and this vapor pressure curve has high relevance for the petroleum industry. At the critical point, the gas and liquid properties are identical. Beyond the critical point, the phase transitions occur without discontinuous changes in the fluid properties. In the region with pressure and temperature higher than the critical point, the fluid is called supercritical.

Figure 2:
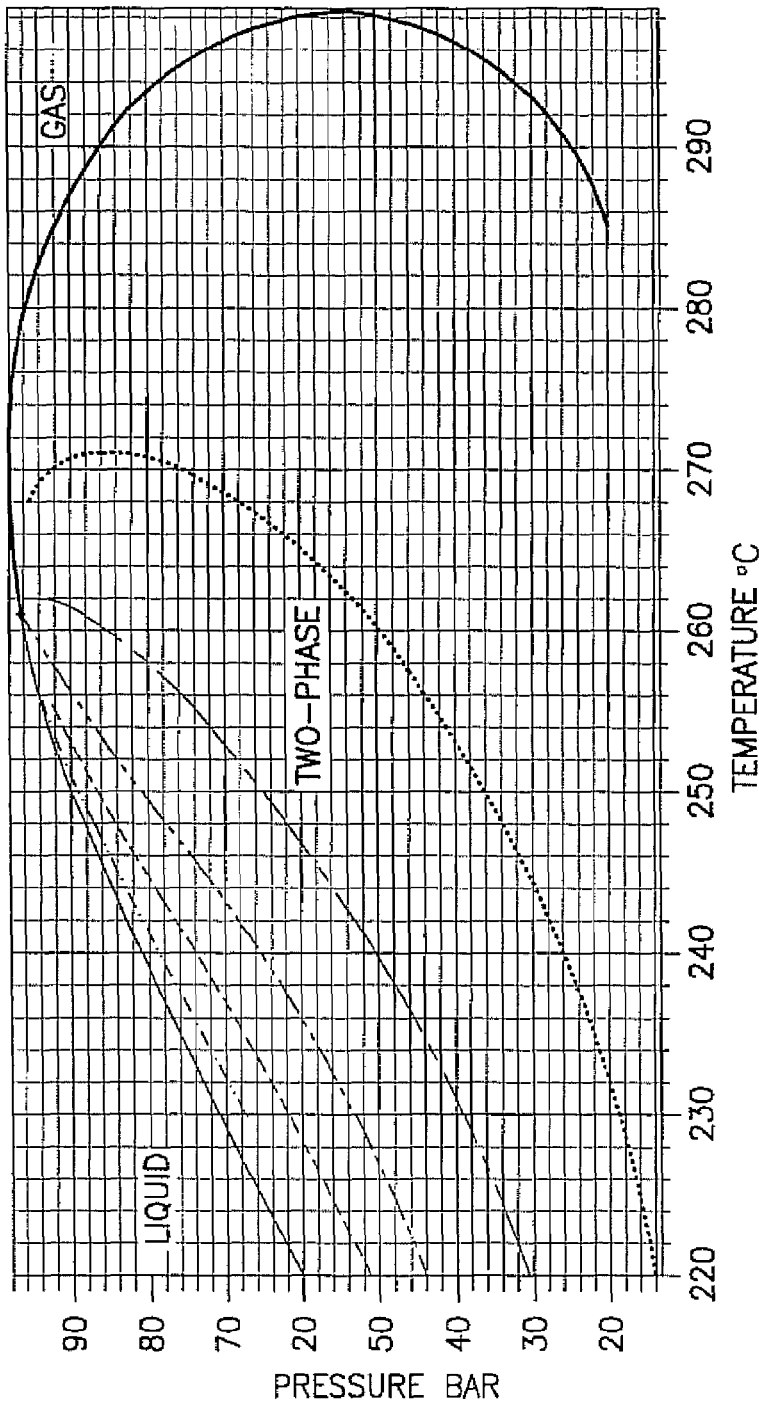
FIG. 2 is a pressure-temperature diagram for a hydrocarbon mixture which shows a bubble line, dew line and critical point for the mixture.

Petroleum fluids (oil and gas) are mixtures of multiple hydrocarbon components (i.e., NC>2) with a complicated phase behavior. When two phases are present, NF>2, and the pressure and temperature conditions under which the two phases exist is represented by an area enclosed by an envelope in a P-T diagram. FIG. 2 shows the P-T phase diagram for a hydrocarbon fluid with composition listed in Table 1.

TABLE 1

| Component | Mole Fraction |
|---|---|
| C1 | 0.7102 |
| C2 | 0.1574 |
| C3 | 0.0751 |
| i-C4 | 0.0089 |
| n-C4 | 0.0194 |
| i-C5 | 0.0034 |
| n-C5 | 0.0027 |
| C6 | 0.0027 |
| C7+ ($\gamma$ = 0.7, M = 103) | 0.0003 |
| CO2 | 0.0167 |
| N2 | 0.0032 |

In FIG. 1, the bubble and dew curves of the pure component coincide. In the case of a mixture, such as the one presented in FIG. 2, the two curves enclose the two-phase region and meet at the critical point. The lines within the envelope correspond to different mole fractions of vapor (V) and, thus, the bubble line corresponds to V=0 and the dew curve has V=1. It is important to note that the fluid composition is constant in FIG. 2.

As is seen in FIG. 2, the left-most line represents the bubble curve of the mixture. For pressure and temperature conditions above the bubble curve, the fluid is in the liquid phase. If pressure is decreased at a constant temperature below the critical temperature (Tc) (i.e., the temperature at the critical point that marks the delineation between the bubble line and the dew line and where the densities of the gas and liquid are equal and meniscus that exists between phases has vanished), the "first" gas bubble will form at the bubble point pressure. In FIG. 2, the right-most line is called the dew curve. Pressure and temperature conditions beyond the dew curve correspond to a single gaseous phase.

The phase envelope is characterized by three properties: the cricondenbar, the cricondentherm and the critical point. The cricondenbar is the highest pressure at which the two phases exist (in FIG. 2 this is approximately 98 bar); the cricondentherm is the highest temperature at which the two phases are present (in FIG. 2 this is approximately 298° C.); and the critical point is the point where the dew line and the bubble line meet and the fluid phases coalesce. In the vicinity of the critical point the classical (e.g., cubic) equations of state (EOS) cannot provide accurate (within a few degrees C. of critical temperature) predictions of the thermodynamic properties of a fluid without recourse to a cross-over model. The critical point of this mixture is shown in FIG. 2 at a pressure of 96 bar and temperature of 260° C.

Equations of state (EOS) describe mathematically the phase behavior of a fluid by relating three intensive properties of matter: pressure, temperature, and molar volume. A basic EOS is the ideal gas equation (1) shown below.

$$P = \frac{RT}{V_M} \quad (1)$$

Most equations of state used in the oil industry are derivatives of van der Waals equation. These cubic equations were developed to deal with phase equilibria of complex multi-component mixtures. The general form of these equations is:

$$P = RT/[V_M - b_1(T)] - a(T)/[(V_M + b_2(T))(V_M + b_3(T))] \quad (2)$$

where $V_M$ is the molar volume, T is the temperature, and R is the universal gas constant. The first term in the right side of Equation 2 represents the correction to the molar volume due to the volume occupied by the molecules. The second term represents the contribution to the pressure due to the attraction of the molecules as a function of temperature.

One drawback related to using cubic equations of state to characterize a fluid is that the equations provide only rough predictions of liquid density (i.e., the predictions may be in error by at least 10%). However, a simple empirical correction, known as the volume translation, has been devised that improves this without affecting the phase equilibria predictions. This correction is usually determined by adjusting a coefficient to measured densities. There are other, more complex, equations of state such as the well-known Benedict-Webb-Rubin equations. These equations can require significant processing power depending on the complexity of the fluid. Thus, in most oilfield applications the cubic EOS are used. For purposes of the present disclosure, the cubic EOS, a more complex EOS, and/or continuous thermodynamic models may be used.

Known methods of determining the dew and bubble curves with equations of state are well documented; see, e.g., Michelsen, M. L., "Calculation of Phase Envelopes and Critical Points for Multicomponent Mixtures", Fluid Phase Equilibria, 4, 1980 (pp. 1-10), which is hereby incorporated by reference herein in its entirety. Use of the cubic equation of state to determine the dew and bubble curves requires knowledge of the critical temperature, critical pressure, and acentric factor ($\omega$) for each of the components, along with the binary interaction parameters ($b_{ij}$) (which may be set to zero if unknown and may result in a reduction in precision of the prediction). The algorithm required to determine the bubble point, which is essentially identical with that required for the dew point, with an equation of state for both phases has been documented in the literature; see, e.g., Michelsen, M. L. id. Essentially, this requires that the composition of the liquid and either the pressure or temperature be fixed and then for an assumed temperature and gas mole fraction the fugacity is calculated with the EOS model. These values are then used to calculate the equilibrium ratio. The process is iterated until the sum of the gaseous mole fractions is equal to unity.

For the case when some fluid components are grouped, schemes can be used to split a grouped composition into individual components at a mole fraction. These procedures, which have been documented in the literature, may increase the accuracy of the predictions from a particular equation of state.

Certain parameters of the selected EOS may also be tuned to additional physical measurements (e.g., measured thermophysical properties) or prior knowledge to obtain a more representative model. If, for example, a measurement of the bubble point pressure of a sample is available, the information is incorporated to fit the selected equation of state at this point. Model parameters that can be tuned include critical pressure, critical temperature, and acentric factor ($\omega$) of each component, binary interaction coefficients ($b_{ij}$), and/or the molar composition of the mixture. For cubic EOS, which poorly represent the density of liquids, a measurement of density is desirable to determine the volume correction factor and, thus, permit prediction densities with an uncertainty of better than 10%.

Uncertainty in phase calculations is associated with the error involved by the use of an EOS to model the fluid behavior, the uncertainty in the composition of the fluid measured with the downhole tool, and the use of pseudo-components to represent groups of hydrocarbon fractions. Therefore, in the examples described herein, the calculations may be made in a probabilistic framework and an estimate of the uncertainty in the calculated phase behavior may be reported with the result. As a result, process decisions may be made in real-time by computerized systems or operators.

In the special case that the composition and other physical property measurements obtained with the MDT tool correspond to conditions near to critical, the uncertainty in the fluid properties calculated with a cubic equation of state are necessarily higher. However, the information that the fluid is near critical is already of great value. In particular, determining which side of the critical point (i.e., whether the fluid is a near critical liquid or near critical gas) is useful data for exploration and production decisions. For example, a near critical gas may show retrograde behavior in the production tubulars while a near critical liquid will have a bubble pressure.

To demonstrate the performance of the proposed analysis scheme, the composition listed in Table 1 for which the phase boundary is shown in FIG. 2 was taken as a starting point. The components of Table 1 were then grouped according to the groups that are available from the MDT CGA analysis. Thus two groups were formed to represent the fractions C2 to C5 and C6+; i.e., the mole fractions of the components C2 through C5 were combined, and the mole fractions of C6 and larger carbon chains were combined. The phase equilibrium calculations were repeated with this CGA pseudo-composition and the P-T section that resulted is shown in FIG. 3.

Figure 3:
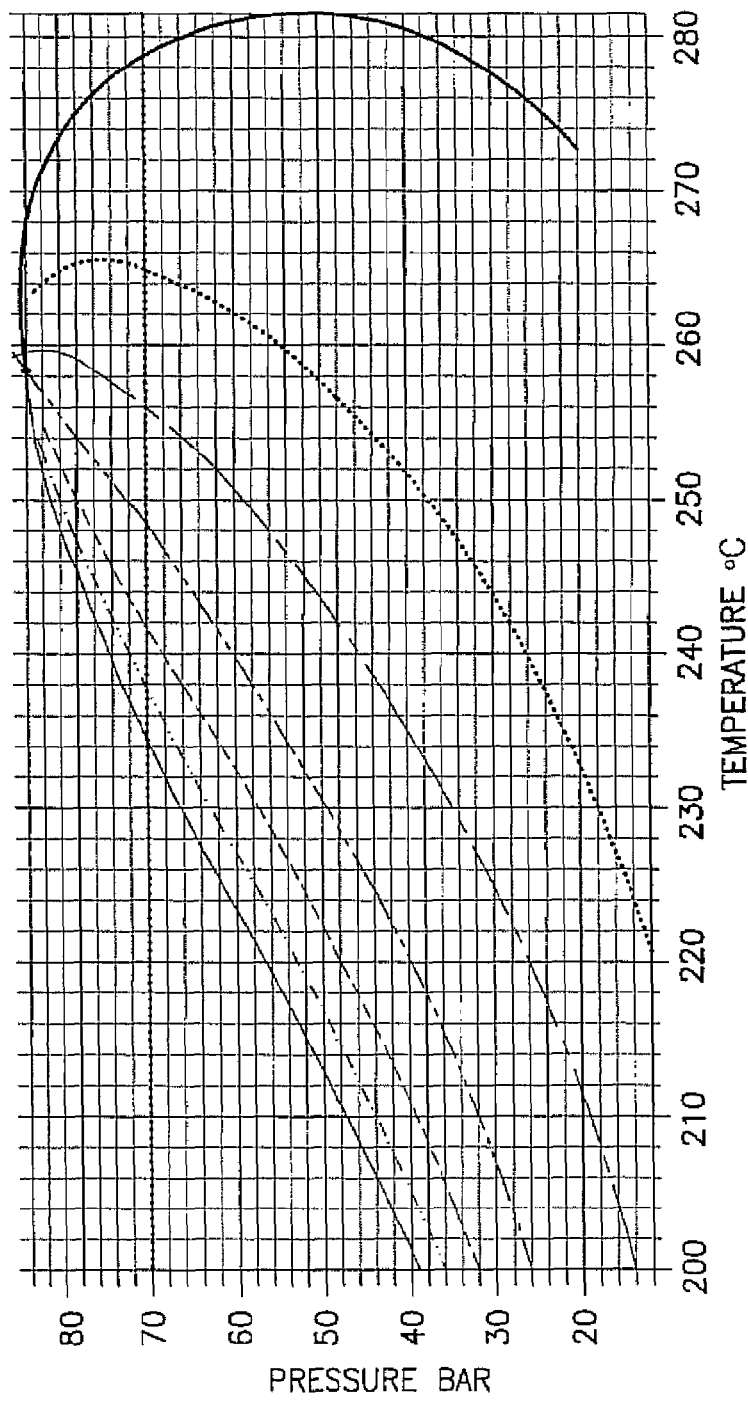
FIG. 3 is a pressure-temperature diagram for a pseudo-composition of hydrocarbons.

For the new pseudo-composition, it is seen in FIG. 3 that the cricondenbar is at pressure of approximately 87 bar, the cricondentherm is at a temperature of about 282° C. and the critical point is at a pressure of approximately 86 bar and a temperature of about 258° C. These calculated values are, in general, a little lower than those shown in FIG. 2 for the extended composition listed in Table 1. When comparing the values obtained with the pseudo-component analysis with the values determined for the extended composition, the pseudo-component cricondenbar is about 12% lower, the cricondentherm about 5% lower and the critical pressure about 11% lower, while the critical temperature is essentially invariant (i.e., within about 1%). Although this comparison has been performed for only one, typical fluid, the results indicate that the maximum pressure and temperature of the phase diagram estimated with the pseudo-composition can be useful in defining (along with an estimated error) the maximum pressure and temperature drops that the fluid can withstand and remain single phase. Perhaps more notable is the very small variation in predicted critical temperature. This implies that the CGA pseudo-component analysis can be used to distinguish the fluid type (e.g., liquid or gas) solely on the basis of a comparison of the calculated critical temperature and the actual reservoir temperature.

Once the model of the fluid is defined, the following properties can be computed: surface tension between phases, viscosity of each phase, Condensate-Gas ratio (CGR) or Gas-Oil ratio (GOR), density of each phase, volumetric factors and compressibility, heat capacity, and saturation pressure (bubble or dew point). Thus, the EOS can be solved to obtain the saturation pressure at a given temperature. The density, gas-liquid ratios, and volumetric factors are byproducts of the EOS. Other properties such as heat capacity or viscosity are derived from the other properties in conjunction with information regarding the fluid composition.

When any of these properties is measured directly or indirectly by the MDT tool or any other logging technique, or is available from prior knowledge, it can be used to validate the EOS models or adjust the parameters within the EOS. The latter is at the user's discretion but may be useful in estimating the uncertainty arising from the method used to calculate the phase envelope.

Furthermore, the properties measured and computed using the example methods and apparatus described herein can be used in conjunction with other reservoir evaluation techniques for a compositional numerical simulation of the flow and production behavior of the reservoir.

Figure 4:
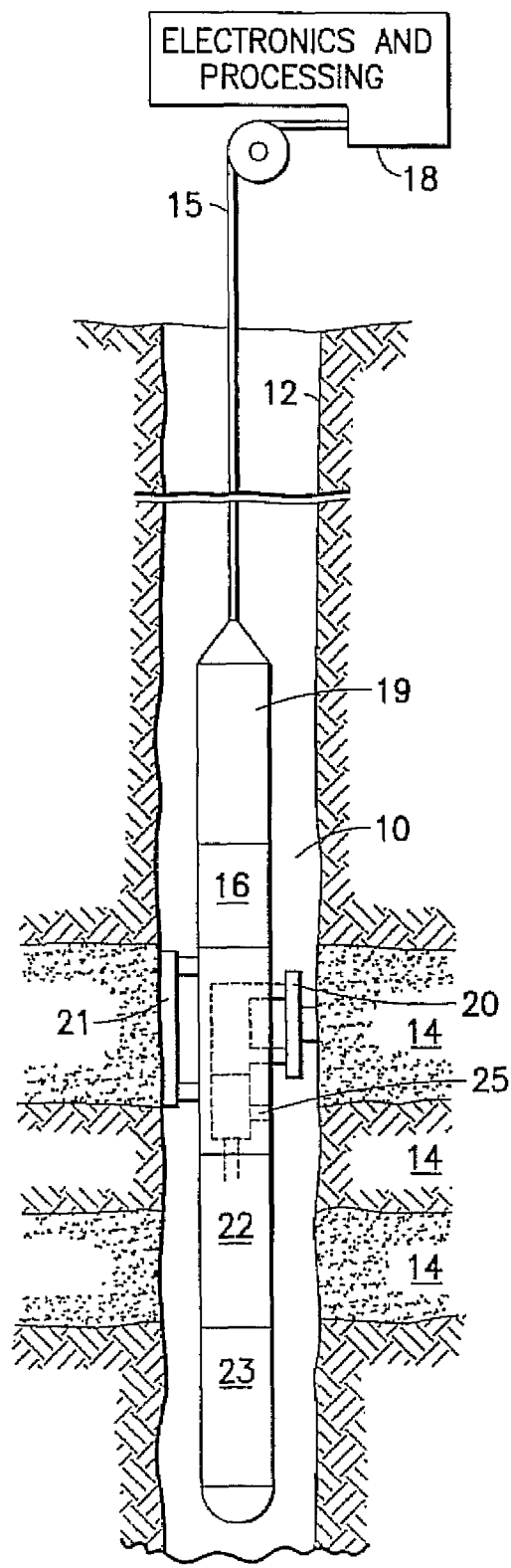
FIG. 4 is a diagram of an example apparatus that may be used to implement the example methods.

Turning now to FIG. 4, an example apparatus that may be used to implement the example fluid characterization methods described herein is shown. In particular, a borehole tool 10 is suspended in the borehole 12 from the lower end of a typical multiconductor cable 15 that is spooled in a usual fashion on a suitable winch (not shown) on the formation surface. The cable 15 is electrically coupled to an electrical control system 18 on the formation surface. The tool 10 includes an elongated body 19 that encloses the downhole portion of the tool control system 16. The elongated body 19 also carries a selectively extendable fluid admitting assembly 20 and a selectively extendable tool anchoring member 21, which are arranged on opposite sides of the tool body, respectively. The fluid admitting assembly 20 is equipped for selectively sealing off or isolating selected portions of the wall of the borehole 12 such that pressure or fluid communication with the adjacent earth formation 14 is established. Also included with tool 10 are sensors or other means for determining the downhole pressure and temperature (not shown) and a fluid analysis (e.g., optical) module 25 through which the obtained fluid flows. The fluid may thereafter be expelled through a port (not shown) or may be sent to one or more fluid collecting chambers 22 and 23, which may receive and retain the fluids obtained from the formation. Control of the fluid admitting assembly, the fluid analysis section, and the flow path to the collecting chambers is performed by the electrical control systems 16 and 18. As will be appreciated by those skilled in the art, the electrical control systems may include one or more microprocessors or other processors or processing units, associated memory, and other hardware and/or software.

Using the apparatus of FIG. 4, a sample of formation fluid was obtained at a measured reservoir pressure and temperature, and the related information was processed with the CGA module/algorithm. The CGA module measures absorption spectra and translates them into concentrations of several molecular groups in the fluids of interest. The CGA module of the MDT tool provides measurements of the concentrations of methane ($CH_4$), a group containing ethane, propane, butane, and pentane fractions ($C_2H_6$, $C_3H_8$, i-$C_4H_{10}$, n-$C_4H_{10}$, i-$C_5H_{12}$, n-$C_5H_{12}$), a lump of hexane and heavier components ($C_6H_{14}+$), and carbon dioxide ($CO_2$), from which molar or weight fractions can be calculated. The (pseudo-) composition determined from the CGA is set forth in Table 2.

TABLE 2

| | Mass Fraction (%) |
|---|---|
| CO2 | 3.5 |
| C1 | 41.1 |
| C2–5 | 22.0 |
| C6 | 33.4 |

Figure 5:
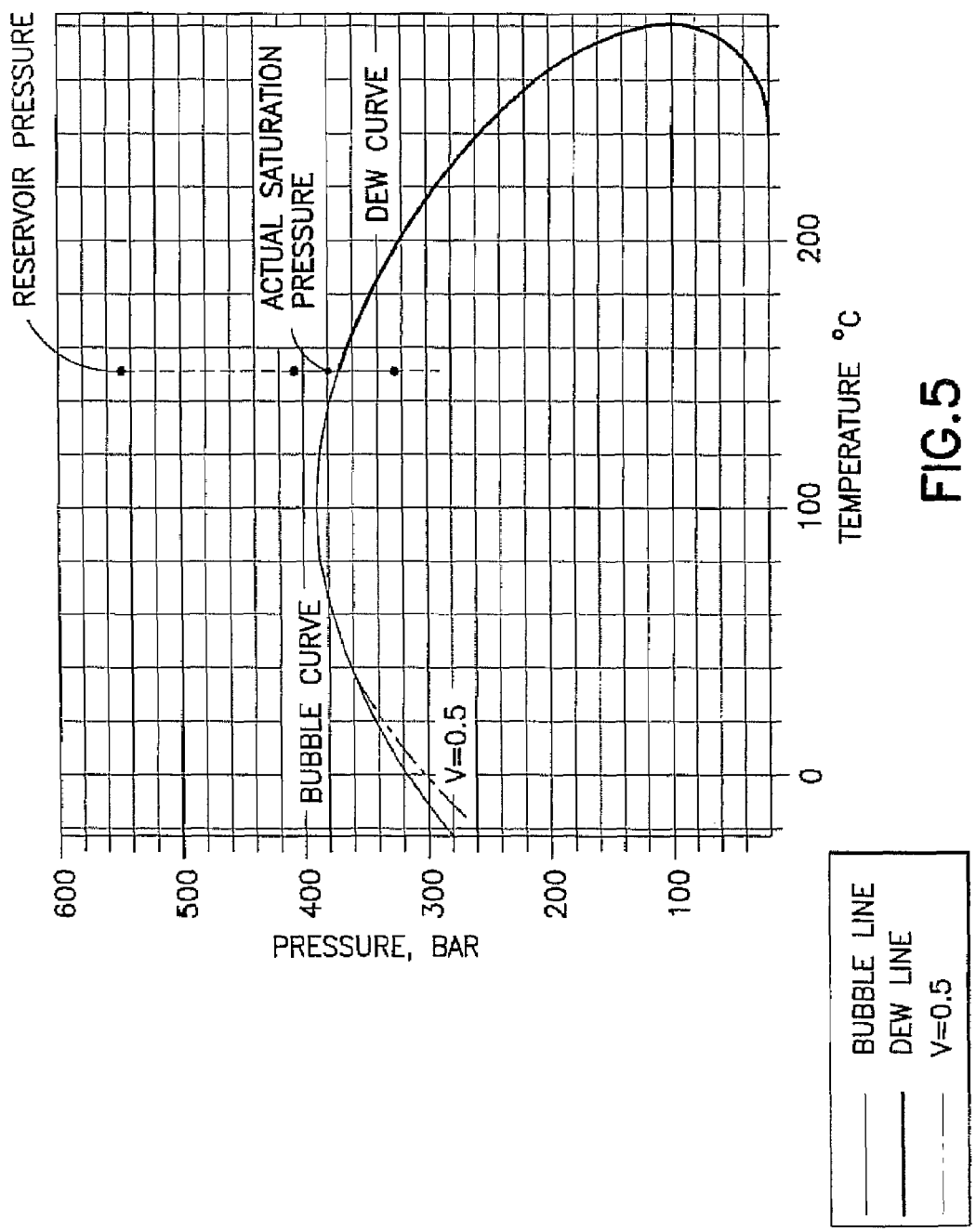
FIG. 5 is a pressure-temperature diagram for a pseudo-composition of hydrocarbons as determined by the CGA module of an MDT tool.

From this composition, the phase diagram of FIG. 5 was obtained.

The reservoir pressure and the actual saturation pressure measured in the laboratory are also plotted in FIG. 5. It can be observed from FIG. 5 that the type of fluid in the reservoir (which was measured to be at a pressure of about 550 bar and temperature of 156° C.) is a retrograde condensate because that pressure/temperature combination is to the right side of the critical point and above the dew curve. As will be discussed hereinafter, this information is valuable because it dictates the considerations to be taken while sampling.

With the fluid characterized as above, the saturation pressure value calculated with the cubic EOS at 156° C. is 372 bar. Using a confidence interval of ±10% represented by the dark circles, the person in charge of the sampling would be advised not to lower the pressure below 410 bar.

For the particular fluid sampled by the apparatus described herein, a laboratory compositional analysis was available and is shown in Table 3:

TABLE 3

| Component | Mole Fraction (%) |
|---|---|
| N2 | 0.51 |
| CO2 | 4.25 |
| C1 | 72.94 |
| C2 | 8.28 |
| C3 | 4.21 |
| iC4 | 0.70 |
| nC4 | 1.43 |
| iC5 | 0.51 |
| nC5 | 0.61 |
| C6 | 0.74 |
| C7 | 1.11 |
| C8 | 1.14 |
| C9 | 0.69 |
| C10 | 2.88 |

Figure 6:
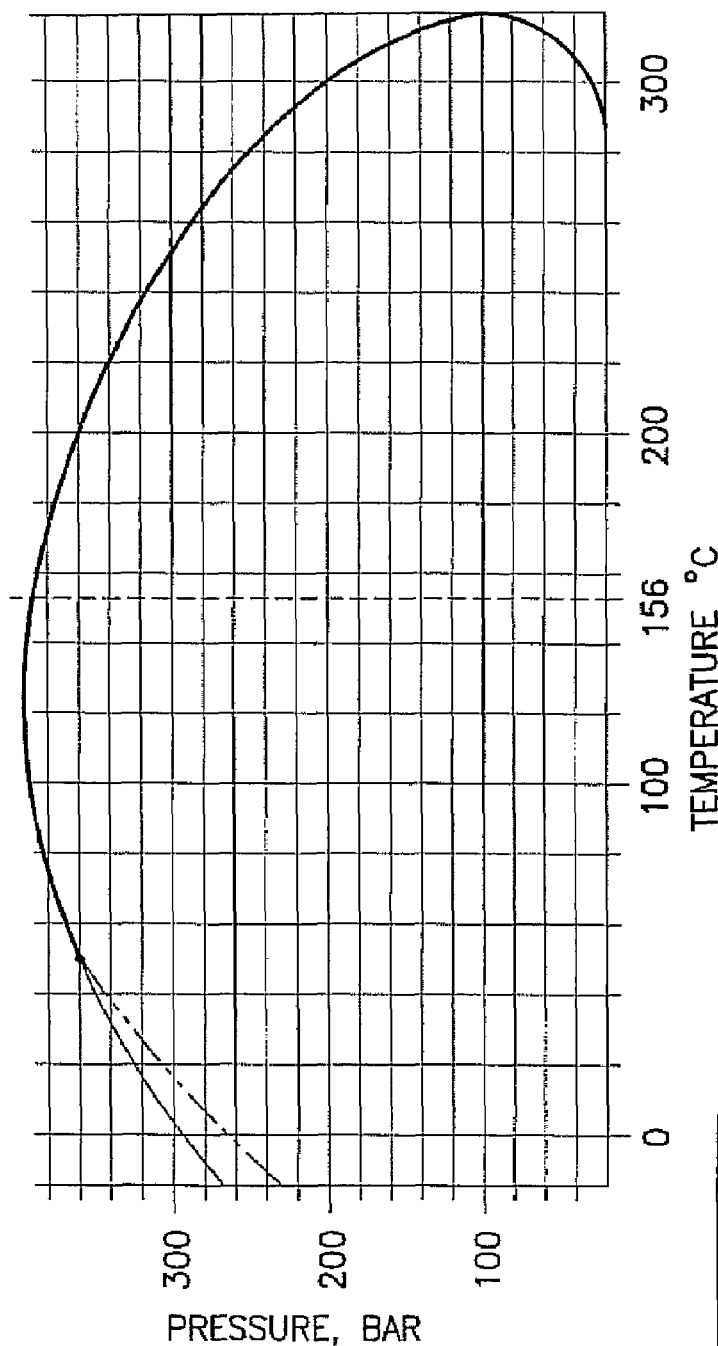
FIG. 6 is a pressure-temperature diagram for the actual composition of hydrocarbons utilized in generating FIG. 5.
Figure 7A:
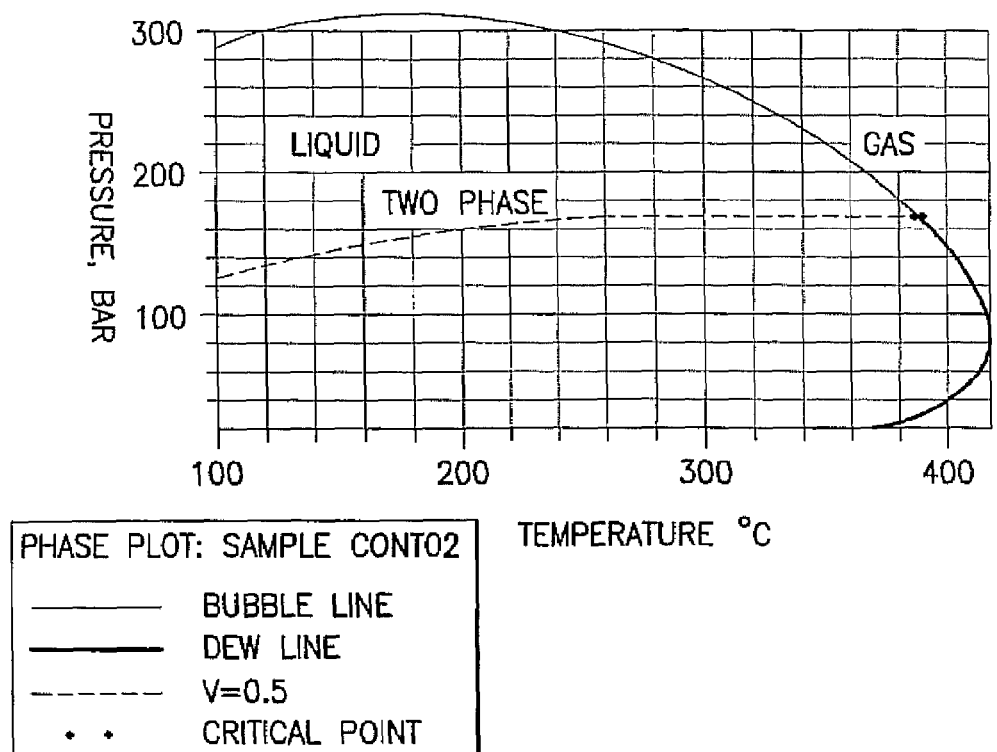
FIGS. 7a-7f are pressure-temperature diagrams for the actual composition of hydrocarbons utilized in generating FIG. 5 but with varying mole fractions of mud filtrate contaminating the sample.
Figure 7B:
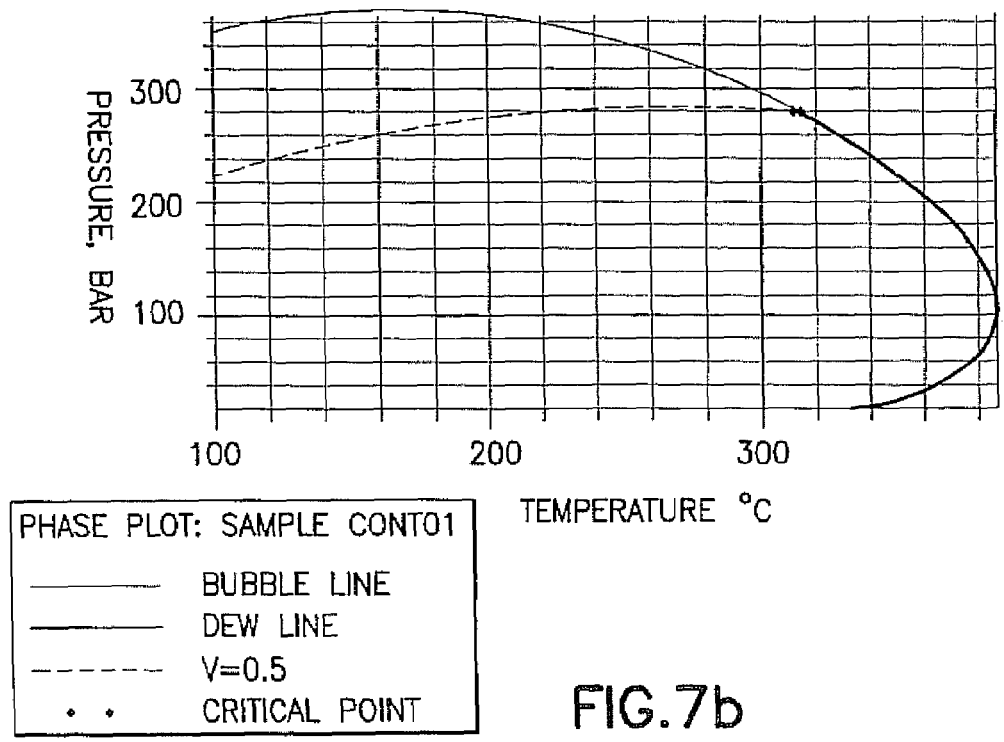
Figure 7C:
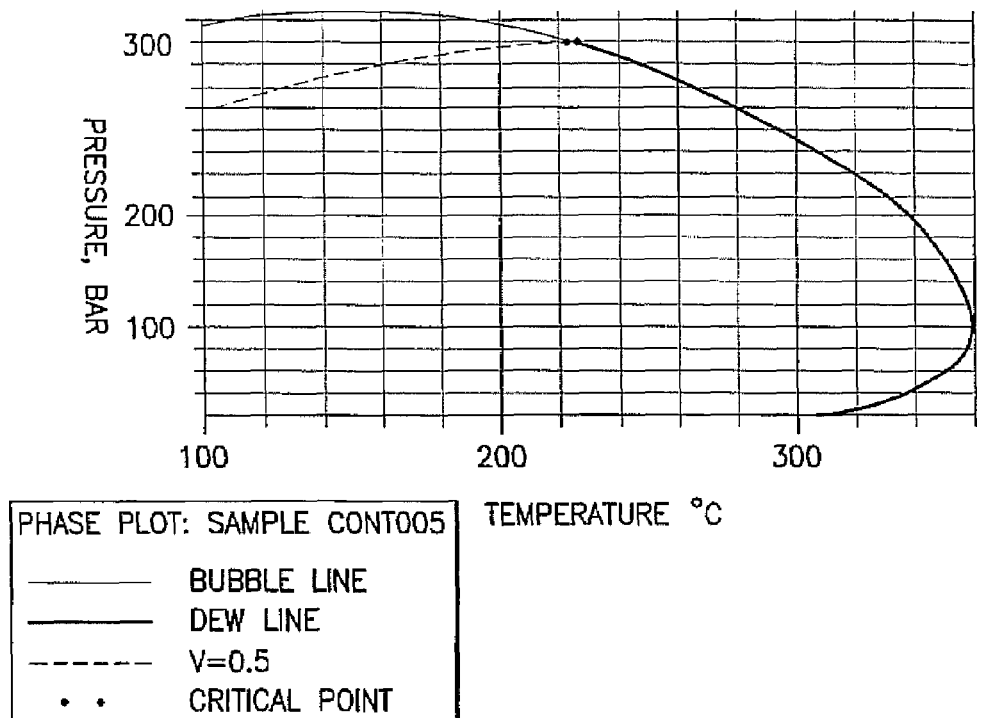
Figure 7D:
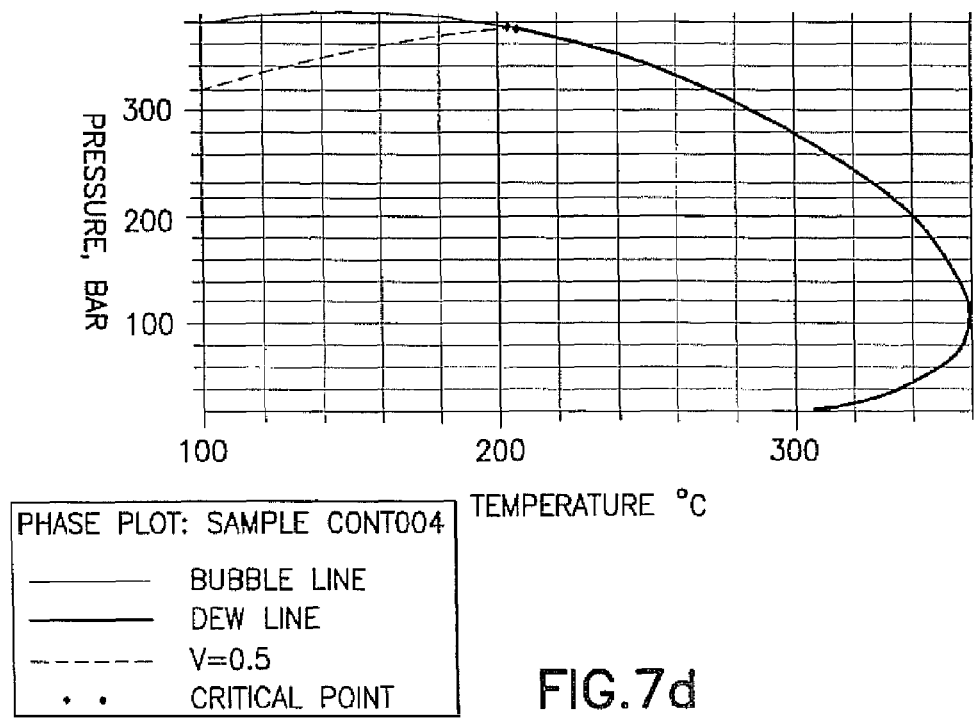
Figure 7E:
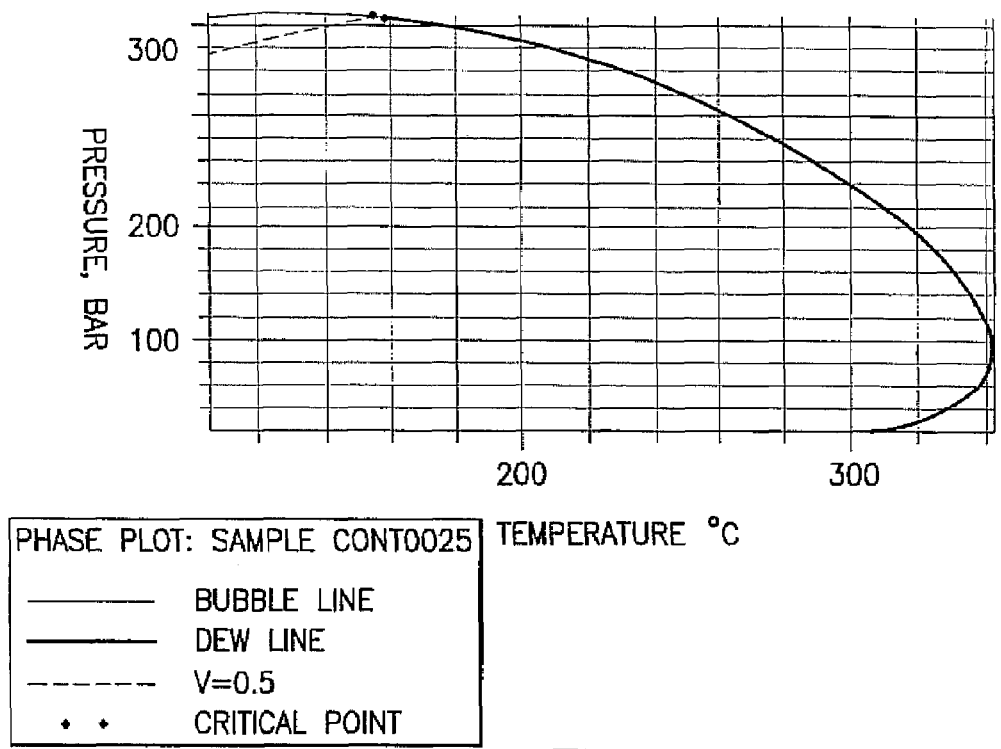
Figure 7F:
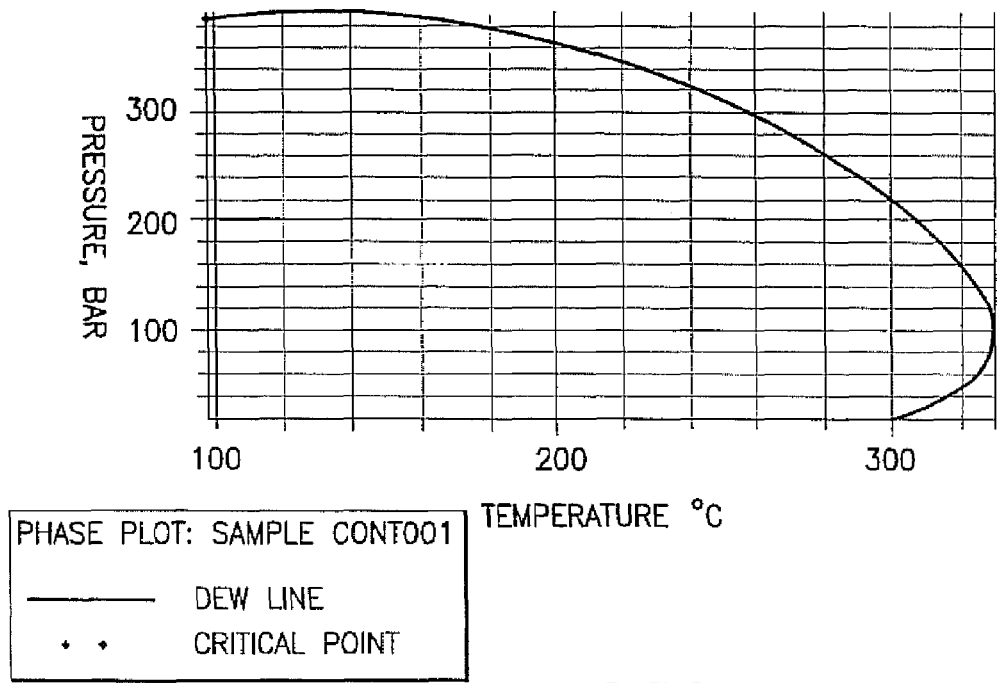

With the components of Table 3 as detailed, a phase diagram was generated and is shown in FIG. 6. As may be seen from FIG. 6, at a temperature of 156° C., the actual saturation pressure of the obtained fluid is 389.5 bar. This point is shown on the plot of FIG. 5 and falls within the confidence interval shown.

According to one aspect of the examples described herein, the generation of phase plots can be used to help determine the effect of borehole mud contamination on the obtained fluid sample. In particular, a tool such as shown in FIG. 4 is introduced into the borehole and stationed at a desired borehole depth, which is typically selected based on an evaluation of the reservoir with open-hole logs in zones where it is expected to find a single-phase fluid (e.g., oil or gas). The tool probe enables hydraulic communication with the reservoir, and fluids are pumped out through the tool and analyzed in the optical module of the borehole tool. The first composition measurements are obtained and usually correspond to a highly contaminated fluid from the near wellbore region where drilling fluid (e.g., an oil-based mud) filtrated into the reservoir and mixed with the native fluids (including, e.g., hydrocarbons). Quantitative estimates of contamination (i.e., the fraction of contamination) can be determined using algorithms that utilize near infrared optical analysis of samples obtained by the MDT such as disclosed in U.S. Pat. No. 6,350,986 to Mullins et al., and U.S. Pat. No. 6,274,865 to Schroer et al., both of which are hereby incorporated by reference herein in their entireties. The contamination estimate is equivalent to the mass fraction of contaminant in the oil-based-mud-filtrate/formation-fluid mixture.

The initial composition measurement of the contaminated sample is used to generate a phase diagram based on calculations performed with an equation of state. Knowing the fraction of contaminant in the mixture, the measured contaminated composition is inverted to obtain an estimate of the uncontaminated fluid. For example, if the compositional measurement determines the fraction of liquid in the sample along with some compositional analysis of gaseous components, then all of the contamination is assigned to the liquid composition, and the fraction of contamination may be subtracted from the liquid to give an estimate of the composition of the virgin fluid. The virgin fluid composition estimation can then be used to predict the phase diagram of the pure phase.

As fluids are pumped through the optical module of the MDT, the composition of the fluids is constantly being determined. Typically, as sampling progresses, progressively cleaner (i.e., less contaminated) samples are obtained. The phase diagrams can be generated continuously and the compositions inverted to estimate the uncontaminated sample based on the fraction of contaminant. These estimates should be in agreement with the initial estimate of the virgin fluid composition. By continuously finding estimated uncontaminated compositions and comparing to previous determinations, the contamination measurement can be validated.

The impact of contamination on various measurements and determinations made therefrom may be seen with reference to FIGS. 7a-7f. FIGS. 7a-7f show P-T diagrams for the sample set forth above in Table 3 but contaminated with different amounts of a mud filtrate composed of 50% nC16 and 50% nC18 (molar fractions). FIGS. 7a to 7e show the diagrams obtained for this mixture at different proportions (molar fractions) of the contaminant. For a 20% mole fraction of filtrate (FIG. 7a), the fluid at the (ambient) reservoir conditions of approximately 550 bar and approximately 156° C. is in the liquid phase, as the critical point for the contaminated mixture is at approximately 172 bar and approximately 390° C. As the contamination decreases from FIG. 7a to FIG. 7b (10% mole fraction of filtrate), FIG. 7c (5% mole fraction of filtrate), FIG. 7d (4% mole fraction of filtrate), and FIG. 7e (2.5% mole fraction of filtrate), the critical point moves towards a lower temperature (e.g., from approximately 390° C. to approximately 157° C.). With 2.5% mole fraction of filtrate, the critical point essentially coincides with the reservoir temperature. At this contamination level it could be erroneously concluded that the fluid in the reservoir is supercritical. At a 1% mole fraction of filtrate (FIG. 7f), the fluid is all in the gas phase at reservoir conditions (i.e., at 550 bar and 156° C.) and the dew pressure at the reservoir temperature is again 389 bar. Thus, it will be appreciated that if correction is not made for contamination, an incorrect determination can be made as to the state of the fluid in the formation.

Those skilled in the art will appreciate that when a large percentage of a formation fluid is constituted from longer carbon chains (e.g., C6+), the mud filtrate composed of 50% nC16 and 50% nC18 will have a smaller effect on the thermodynamic model of the fluid; and when a large percentage of the formation fluid is constituted from methane or short carbon chains, the typical oil-based mud filtrate will have a larger effect on the fluid model.

Figure 8:
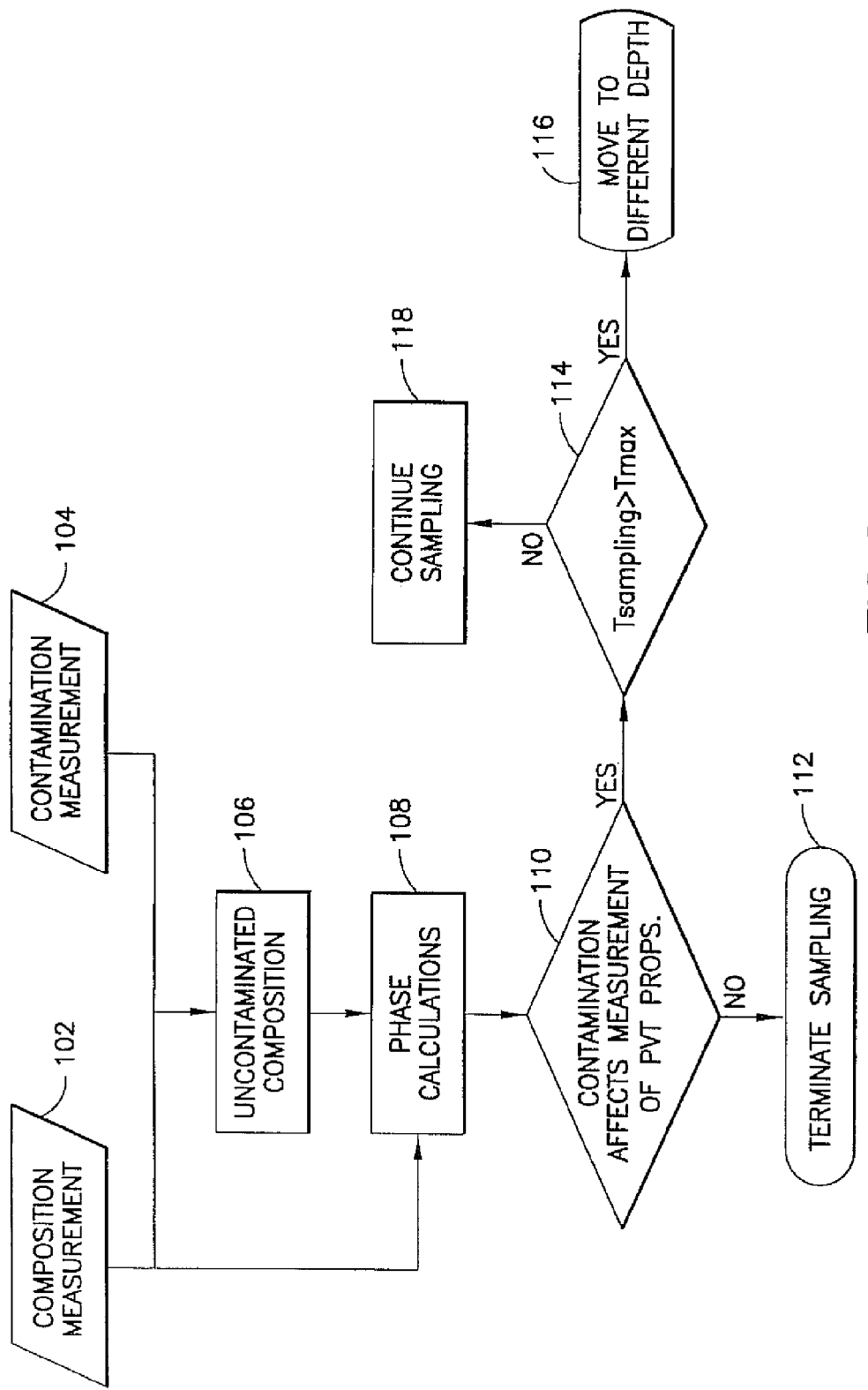
FIG. 8 is a flowchart illustrating the use of phase calculations in determining whether or not to continue sampling.

The provision of a downhole tool that can produce phase diagrams of in-situ fluids and which can account for mud filtrate contamination has numerous applications. For example, the characterization of the fluid sample with respect to its thermodynamic model can be used as a benchmark to determine the validity of the obtained sample, whether to retain the sample, and/or whether to obtain another sample at the location of interest. More particularly, and turning to FIG. 8, after a fluid sample is obtained by the borehole tool, a measurement of the composition or pseudo-composition of the (contaminated) sample is made at 102 and a measurement of the level of contamination is made at 104. With both measurements, and given knowledge of the constituents of the contaminants, determination of the constituents of the virgin (uncontaminated) fluid is found at 106. Utilizing equations of state, phase calculations of both the uncontaminated and the contaminated fluids may be made and compared at 108. The phase calculations may then be compared at 110 at the formation temperature and pressure, in order to determine whether the contamination significantly affects the PVT properties of the fluid. In other words, if the pressure and temperature of the formation are located on same portions of the P-T diagrams for the contaminated fluid and uncontaminated fluid indicating that the fluid is in the same phase in both cases, the contamination may not be considered "significant," and the sampling at that depth in the borehole may be completed at 112 with the storage (if desired) of the obtained sample. On the other hand, if the contamination significantly affects the PVT properties of the fluid, at 114, a determination is made as to whether the sampling time at the depth location in the formation has reached a maximum time. If so, at 116, the tool is preferably moved to a new location for sampling; while, if not, at 118, additional fluid samples may be obtained in the hope that fluid contamination will decrease to a level where it is not significant.

Continuous or multiple sampling, and the processing of data from the continuous or multiple sampling that results in multiple contamination measurements, multiple uncontaminated composition determinations, and multiple sets of phase calculations can be used in several manners. First, as multiple determinations are made of the contamination measurements and the uncontaminated composition, the certainty level with respect to these values increases. The certainty level can be provided along with the actual determination as a "product." Second, as will be discussed hereinafter with respect to FIGS. 10 and 11, in certain circumstances the initial phase calculations can be used to adjust the drawdown pressure in order to obtain a single phase fluid. Third, multiple determinations can be used to predict a contamination clean-up rate which in turn can be utilized in determining whether or not to continue sampling at the sampling location.

Figure 9:
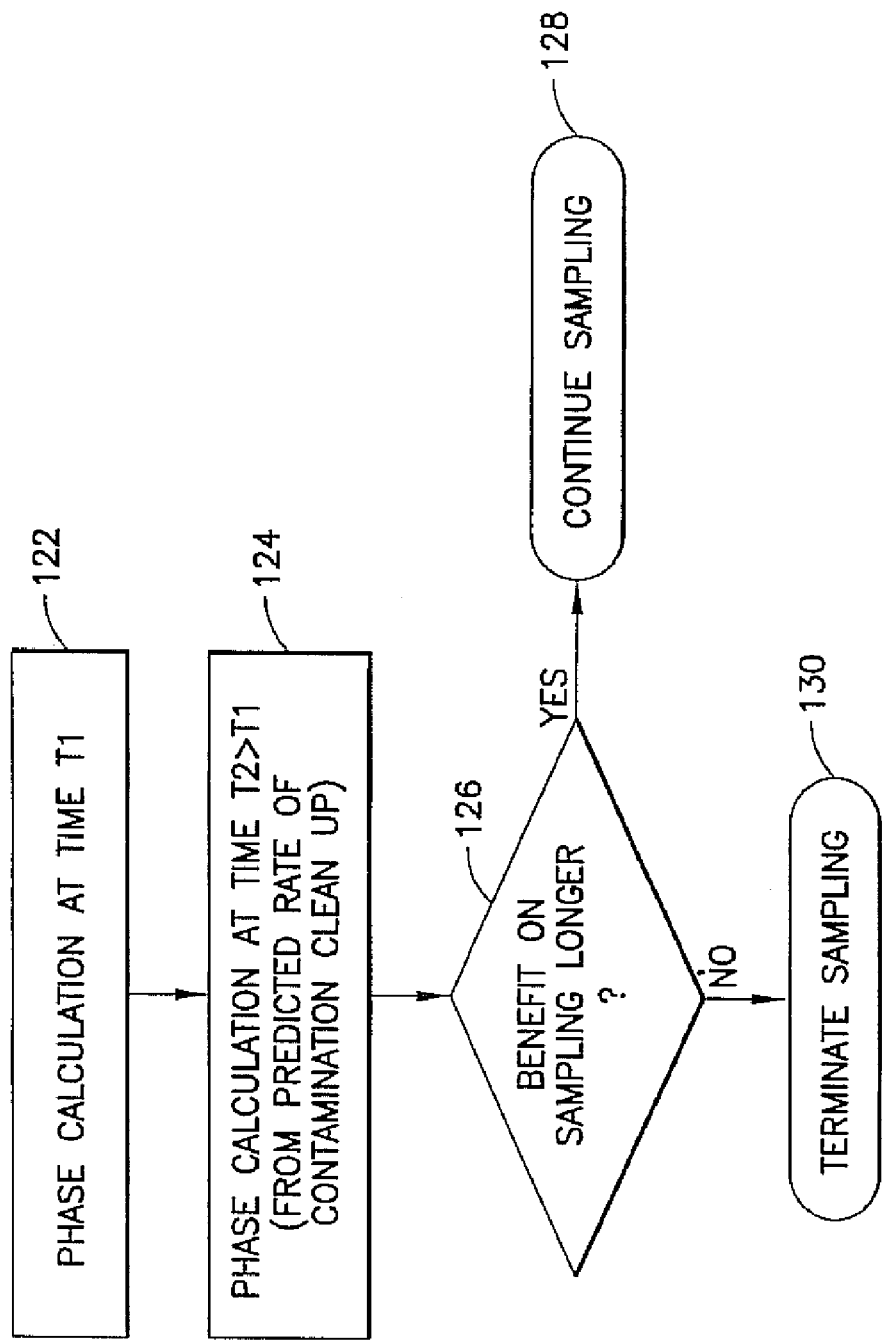
FIG. 9 is a flowchart illustrating the use of phase calculations made over time in a decision regarding whether or not to continue sampling.

Turning to FIG. 9, with a first phase calculation having been previously conducted at 122 on a first fluid sample, a second phase calculation is conducted at 124 on a second fluid sample. If desired, third and subsequent phase calculations (not shown) can be conducted on additional fluid samples. Based on the respective phase calculations, a determination is made as to the rate of contamination clean-up. If the rate of contamination clean-up suggests at 126 that an acceptable contamination level will be reached within a suitable timeframe, sampling continues at 128. If not, sampling is terminated at 130. It should be noted that the "acceptable contamination level" correlates to whether the level of contamination will significantly affect the PVT properties of the fluid as discussed above with reference to FIG. 8.

Figure 10:
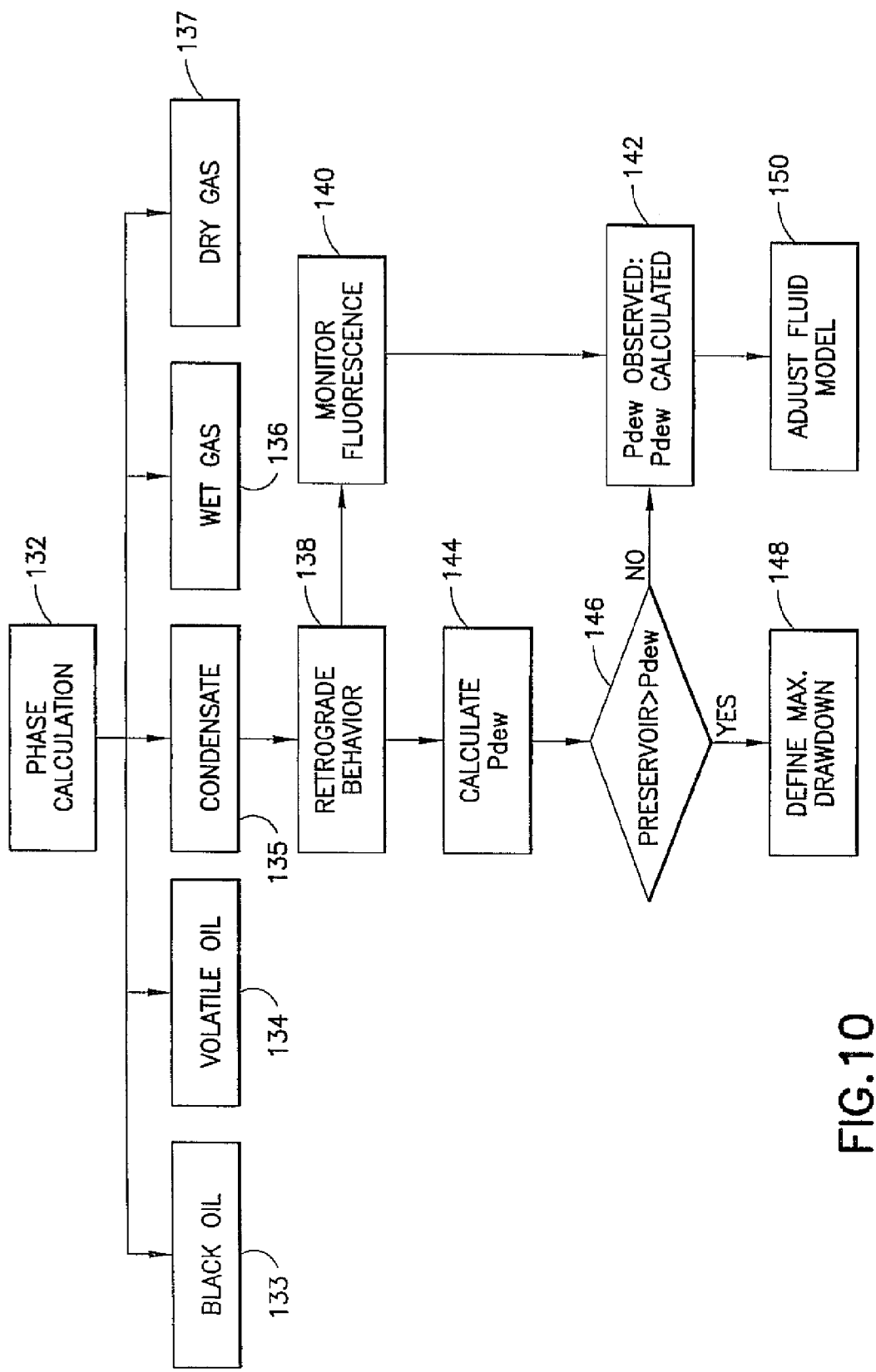
FIG. 10 is a flowchart illustrating the use of phase calculations to define drawdown pressures for retrograde condensates.

As previously suggested, phase calculations can also be used to adjust drawdown (sampling) pressures. As seen in FIG. 10, based on the phase calculations at 132, and also with knowledge of the temperature and pressure of the formation, a determination can be made as to whether the in situ fluid is black oil 133, volatile oil 134, condensate 135, wet gas 136 or dry gas 137. In the case of condensate, if at 138 the fluid being sampled from the formation is a gas (i.e., the condensate is exhibiting "retrograde behavior"), as taught in co-owned U.S. Pat. No. 7,002,142, which is hereby incorporated by reference herein in its entirety, the gas may be monitored for its fluorescence at 140, and its dew pressure observed at 142. Also, at 144, from the phase calculations, the dew pressure Pdew (i.e., the point on the dew curve corresponding to the in situ temperature) can be calculated. If at 146 the in situ pressure of the reservoir Preservoir is greater than the dew pressure, a maximum drawdown pressure drop (i.e., Preservoir-Pdew) is defined at 148 in order to maintain single phase flow into the borehole tool. This maximum drawdown pressure drop may be used in the sampling procedure to adjust the drawdown pressure utilized in obtaining samples. However, if the calculation of Preservoir from the phase calculations is not greater than Pdew, than retrograde behavior should not be observed. Thus, the Pdew calculated at 146 does not equate to the Pdew observed from the monitoring of fluorescence, and the fluid model should be accordingly adjusted at 150 by e.g., choosing different equations of state, adjusting parameters in the EOS, or adjusting the determination of the compositional components.

Figure 11:
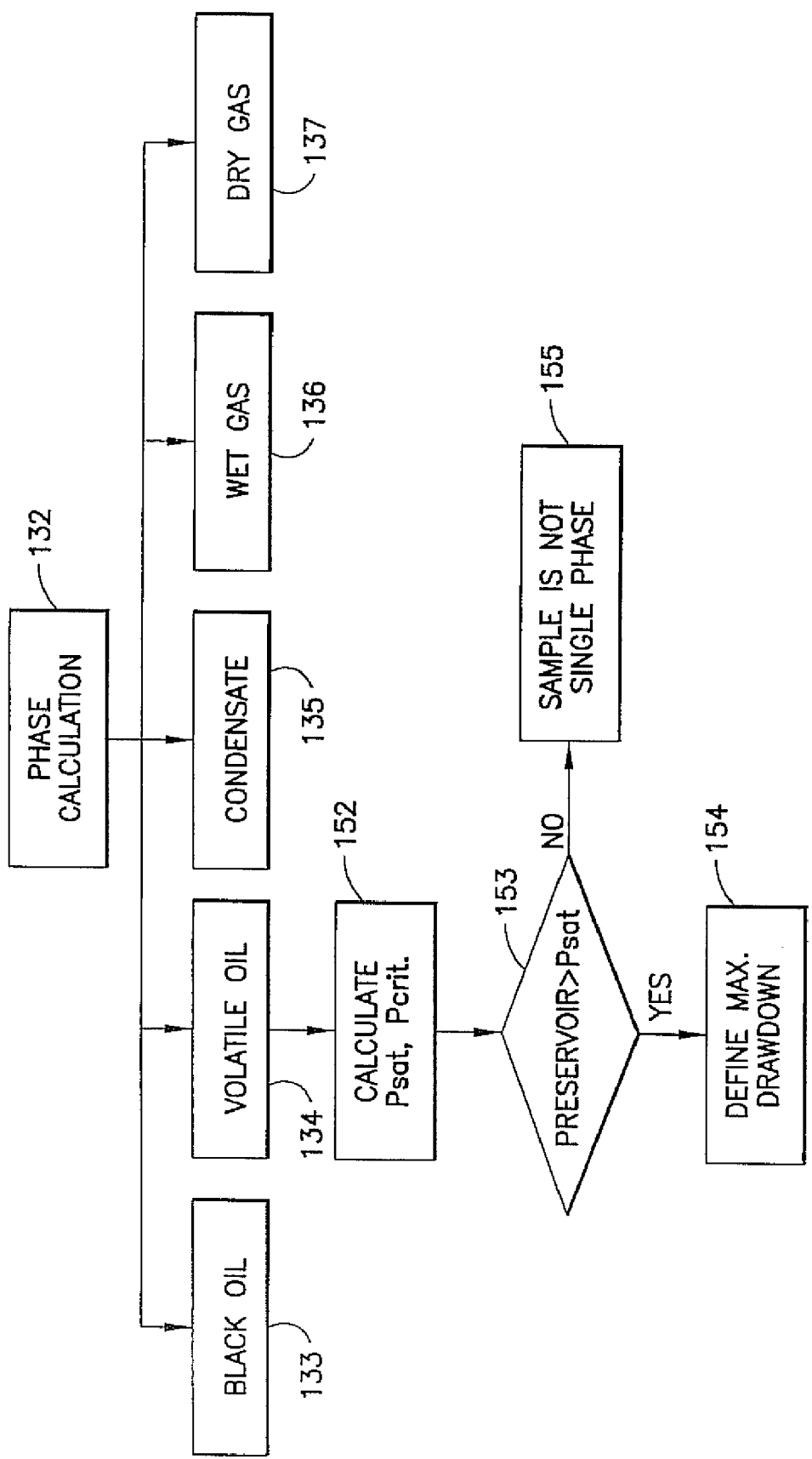
FIG. 11 is a flowchart illustrating the use of phase calculations to define drawdown pressures for volatile oils.

If the phase calculations at 132 suggest that the in situ fluid is volatile oil 134, as seen in FIG. 11, a different set of calculations may be conducted. With volatile oil, at 152 the saturation pressure Psat and optionally the critical pressure are calculated. If at 153 the reservoir pressure Preservoir is greater than Psat, a maximum drawdown pressure drop (i.e., Preservoir-Psat) is defined at 154 in order to maintain single phase flow (i.e., liquid) into the borehole tool. This maximum drawdown pressure drop may be used in the sampling procedure to adjust the drawdown pressure utilized in obtaining samples. In addition, if the drawdown pressure is to be adjusted, other adjustments (such as the contamination cleanup rate—FIG. 9) may be made to the system. However, if Preservoir is not greater than Psat, then the obtained sample should be a two phase sample 155. If desired, this determination can be compared to a determination of phase of the actual sample, and the fluid model accordingly adjusted if the prediction differs from the actual situation. It should be noted that the maximum drawdown pressure drop may also be used in making decisions regarding production of hydrocarbons from the formation.

According to another aspect of the example methods and apparatus described herein, if it determined that the fluid sample was obtained near the bubble line of the sample, a decision may be made to conduct drawdown at different pressure drops in order to find an exact (actual) bubble point. The bubble point may then be used in making decisions regarding production of hydrocarbons from the formation.

It will be appreciated by those skilled in the art that one possible "output" of the example apparatus described herein is one or more P-T diagrams for each obtained sample with or without indications of certainty. In lieu of P-T diagrams, it is possible to provide for each depth of interest a numerical indication of the bubble or dew point at the temperature of the formation at that depth. Likewise, it is possible to simply provide an indication of a pressure under which two phase production would occur. Other possible outputs include, inter alia, density, gas-liquid ratio, and viscosity determinations, as well as evaluations of contamination effects on sample quality and fluid behavior.

The versatility of fluid composition measurements at different borehole depths opens the possibility of gaining a better understanding of the reservoir structure. Knowing the estimated compositional gradient, it is possible to compare the estimated composition at a different depth with the actual measurement at that depth to analyze variations. Abrupt changes in the composition that may or may not be accompanied by changes in the pressure gradient are an indication of vertical discontinuity in the reservoir structure.

Composition measurements along with real time phase calculation at different depths enables the computation and verification of important fluid properties such as saturation pressure, gas-liquid ratios, and liquid drop-out volumes on high quality single-phase samples obtained at downhole conditions without the risk of phase recombination on the formation surface. The variations of these properties with depth can be used as the basis for the construction of a fluid model for the whole reservoir.

A specific situation where fluid composition and phase behavior calculations are of great utility is the analysis of reservoirs containing gas and liquid zones where it is of primary interest to identify if the gas is associated with the liquid. In this case, the bubble point of the liquid hydrocarbon obtained from phase calculations and the compositional gradient give an indication of the communication between the two zones. Specifically, if the oil zone is not near its saturation pressure, then it is most likely not in communication with nearby gas zones. Conversely, if an oil is at its saturation pressure and a gas containing formation is nearby, it is likely that the two zones are in communication.

Another application is the case of thick reservoirs where compositional variations occur due to gravity and temperature gradients. Prediction of gas-oil fluid contacts in these cases is possible from the composition gradient. In reservoirs that span a large range of depths the composition variations can be tested following the previous procedure in selected wells.

The foregoing example apparatus and methods enable relatively rapid downhole characterization of fluids associated with underground or subterranean geological formations. More specifically, some of the foregoing example apparatus and methods are configured to enable the properties (e.g., the thermophysical properties) of formation fluids (e.g., hydrocarbon-based fluids to be extracted or produced from a subterranean formation or reservoir) to be determined quickly (e.g., in real time) using a downhole tool. In particular, in some of the examples described above, formation fluid may be sampled and subjected to a limited compositional analysis (e.g. pseudo-component analysis). This limited compositional analysis determines the chemical composition (i.e., pseudo-composition) of the sample using a relatively limited set of chemical constituents or components. For example, the compositional analysis may measure individually the mole fractions of hydrogen sulfide, carbon dioxide, methane, ethane, propane, as well as other heavier hydrocarbons. However, typically, to enable a more rapid compositional analysis, certain groups of hydrocarbons may be measured simultaneously or lumped together. For instance, in one limited compositional analysis, concentrations of methane, a group containing ethane, propane, butane, and pentane fractions, a group containing hexane and heavier hydrocarbons, and carbon dioxide may be measured.

The results (e.g., pseudo-component concentrations or mole fractions) of the limited compositional analysis can then be used to populate the parameters of a thermodynamic fluid model such as, for example, a cubic equation of state to form an adjusted pseudo-component model for the fluid. In turn, the pseudo-component model for the fluid can then be used to derive various thermophysical properties of the sampled fluid to thereby facilitate the economic evaluation of a fluid reservoir or reserve to be produced, to control the production parameters to enable more effective and efficient production of a reserve, to select optimal well completion, etc.

Thus, the foregoing example methods and apparatus focus primarily on the use of a chemical compositional analysis to generate a mathematical model representing the thermodynamic behavior (e.g., phase behavior or properties) of a formation fluid. As a result, the accuracy of any thermophysical properties of the formation fluid that are determined using the generated model is determined, at least in part, by the accuracy of the limited chemical compositional analysis.

However, as described above in connection with FIGS. 2 and 3 and in more detailed examples below in connection with FIGS. 12, 13, 14a, and 14b, mathematical thermodynamic models of fluids can also be tuned or adjusted using downhole measurements of the physical properties of formation fluids in addition to compositional analysis to provide improved thermodynamic models of the fluids. For example, the use of at least one other physical property to generate a thermodynamic model of a fluid may significantly improve the accuracy of the model and its ability to predict the thermodynamic behavior of a fluid at temperatures and pressures different from the temperatures and pressures at which downhole measurements are made. For example, the measurement of saturation pressure, fluid density, fluid viscosity, heat capacity, and/or any other physical properties of the fluid may provide data that can be used to tune or adjust a thermodynamic model of a formation fluid to provide more accurate predictions of the thermodynamic behavior of the fluid throughout a production process, the economics of a reserve of the fluid, etc. Additionally, the use of continuous thermodynamic models or the thermodynamics of polydisperse fluids can be employed to further improve the accuracy of a compositional model (e.g., a pseudo-component model).

Figure 12:
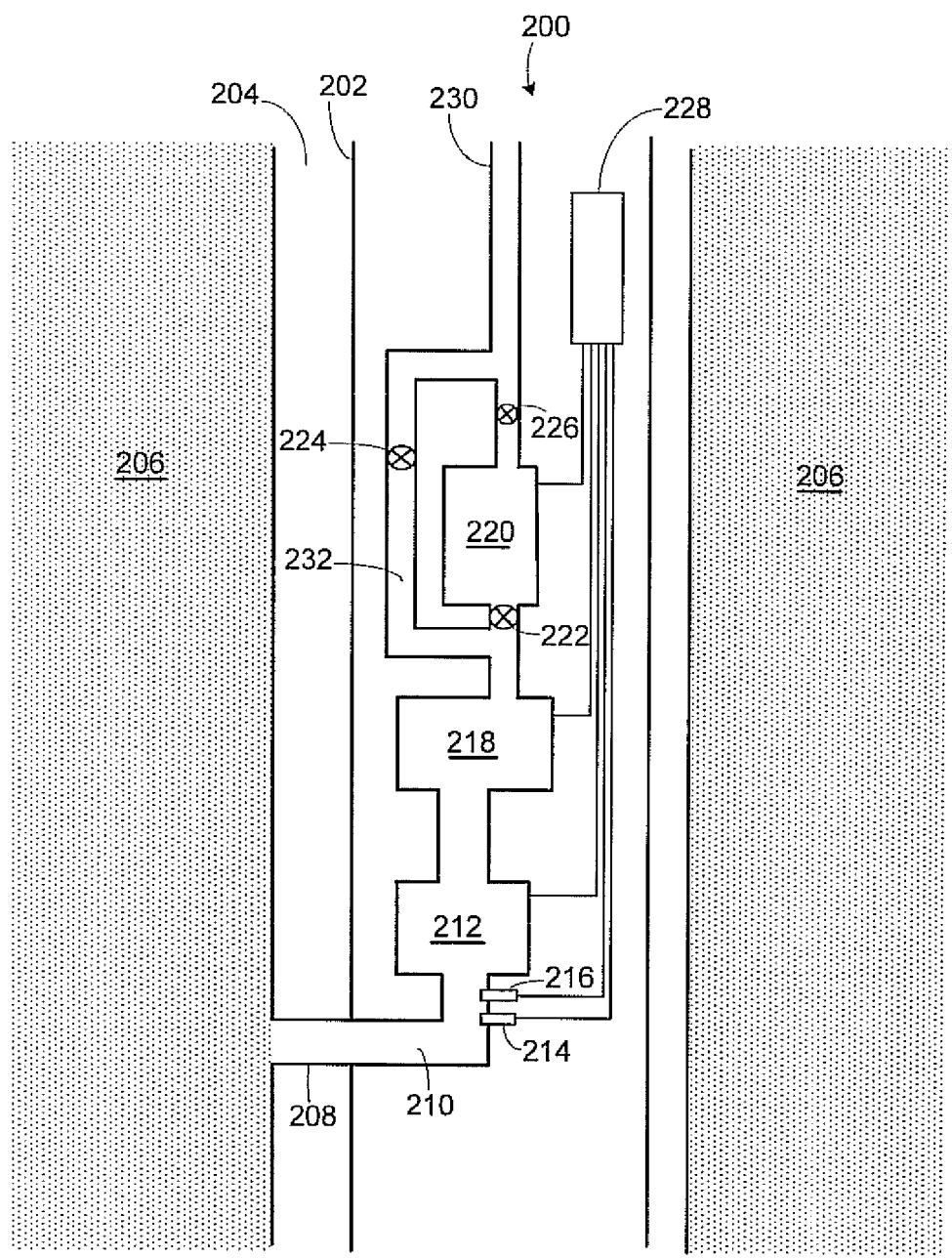
FIG. 12 is another example apparatus that may be used to characterize a formation fluid in situ.

Turning now to FIG. 12, another example apparatus 200 that may be used to perform downhole measurements of a formation fluid and to characterize the formation fluid is depicted. As shown in FIG. 12, a downhole fluid analysis tool 202 is disposed within a borehole 204 that penetrates a geological formation 206. The tool 202 may be disposed in the borehole 204 adjacent the formation 206 using any desired technique and apparatus. For example, the tool 202 may be a wire-line type tool, conveyed via drill pipe, or via any other type of conveyance suitable for disposing the tool 202 in the formation 206. Additionally, as described in more detail below, in addition to being configured to characterize or analyze formation fluid in situ, the tool 202 is also configured to function as a sampling device.

The formation 206 may be, for example, a hydrocarbon bearing reservoir or reserve to be evaluated. In particular, it may be desirable to characterize the hydrocarbon fluids present in the formation 206 to determine the potential economic value of the formation 206, to determine the most effective or efficient manner to produce the formation 206 (e.g., the pressures used in extracting the fluid from the formation as well as other pressures and temperatures throughout the production process), etc.

The tool 202 includes a probe 208 that may be used to extract fluid from the formation 206 and convey the extracted fluid via a flow-line 210 to a first chamber 212. The probe 208 may be a single or dual (e.g., guard) probe, a dual packer, or any other device suitable to enable fluid communication between the tool 202 and the first chamber 212 and to extract fluid from the formation 206. A temperature sensor 214 and pressure sensor 216 are located in the flow-line 210 to enable the measurement of the temperature and pressure of the extracted fluid as it enters the first chamber 212.

The first chamber 212 is configured to determine the chemical composition of the extracted fluid provided via the flow-line 210. More specifically, the chamber 212 may be configured to determine the relative amount of carbon dioxide, hydrogen sulfide, methane, ethane, propane, and/or any other hydrocarbons or groups of hydrocarbons. In addition, the chamber 212 may be further configured to determine the phase or fluid type of the fluid therein such as, for example, by determining whether the fluid is oil, water, and/or gas using, for example, electric permittivity measurements.

The chamber 212 may employ optical spectroscopy devices, gas chromatography devices, mass spectrometry devices, nuclear magnetic resonance devices, and/or liquid-liquid chromatography devices to enable the determination of the chemical composition of the formation fluid in the chamber 212. If, for example, optical spectroscopy devices are used and a relatively simple optical spectrum is measured, the concentration of methane, ethane, propane, carbon dioxide, and a group containing all heavier hydrocarbons can be measured. Such measurements are sufficient to determine the volumetric ratio of gas to oil of the fluid. Such measurements are also sufficient to perform a pseudo-component analysis that can be combined with pressure and temperature measurements (e.g., from the sensors 214 and 216) and fluid models to estimate the thermophysical properties of the fluid.

Fluid passing through the first chamber 212 flows to a second chamber 218, which is configured to measure the density and viscosity (e.g., the Newtonian viscosity) of the fluid therein. Such measurements of fluid density and viscosity can be made while the fluid is relatively still or stagnant within the second chamber 218 or while the fluid is moving or flowing through the second chamber 218. The measurements of fluid density and viscosity made using the chamber 218 can, for example, be combined with the fluid composition information obtained via the first chamber 212 to determine the degree to which the formation fluid is contaminated with drilling fluid.

A third chamber 220 receives fluid from the second chamber 218 and operates in conjunction with first, second, and third valves 222, 224, and 226. The third chamber 220 includes a circulating pump (not shown), a variable volume chamber (e.g., a positive displacement pump), and sensors and other devices to enable the measurement of temperature, pressure, density, viscosity, and phase borders. Sensors and devices to measure temperature, pressure, density, and viscosity are generally well known in the art and, thus, are not shown in FIG. 12 for purposes of clarity and are not described further herein.

In carrying out the measurements and/or other operations associated with the second chamber 218 and the third chamber 220, it may be assumed that these chambers 218 and 220 are at the same temperature as the tool 202. However, if desired, the chambers may be sized and insulated to facilitate the independent heating and cooling of the chambers 218 and 220 to enable measurements at temperatures other than the temperature of the tool 202. Such additional measurement information may be used in connection with regression analyses (e.g., linear or non-linear regression) to provide additional information for use in tuning mathematical models representing the thermophysical properties of a fluid.

The valves 222, 224, and 226, the operation of the chambers 220, 218, and 212, including the measurements made thereby, and the measurements made by the temperature sensor 214 and the pressure sensor 216 may be controlled by an electronics module or unit 228. The electronics unit 228 may include analog and/or digital sensor interface circuitry, signal conditioning circuitry, one or more processing units such as, for example, microprocessors, memory circuits, stored computer code or software, application specific integrated circuits (ASIC's), discrete analog circuits, discrete digital circuits, passive components, etc. In this manner, the electronics module or unit 228 may be used to coordinate the operations of the chambers 212, 218, and 220 and analyze or process the data or information relating to the extracted formation fluid to characterize the thermodynamic behavior of the fluid. Such characterization may include selecting, generating, and/or tuning or refining a mathematical model of the extracted fluid. In turn, the resulting mathematical model of the fluid can be used by the electronics unit 228 and/or a surface computing device to accurately predict or estimate the thermodynamic behavior of the formation fluid at various temperatures and pressures such as, for example, temperatures and pressures that may be desired or used in producing the fluid from the formation 206. For example, the information relating to the predicted or estimated thermodynamic behavior of the fluid in the formation 206 may be used to establish the conditions under which the formation fluid should be extracted or produced to maintain the fluid in a single phase state (e.g., a fluid state), thereby significantly improving the efficiency and economics associated with producing fluid from the formation 206.

While the electronics unit 228 is depicted as being entirely within the tool 202, the operations performed by the electronics unit 228 may alternatively be located elsewhere and/or distributed among multiple locations. For example some or all of the processing activities performed by the electronics unit 228 may be performed at a surface computing device locally or remotely situated relative to the bore hole 204.

In operation, the valves 222, 224, and 226 are opened/closed to flush formation fluid through the chamber 220 and/or to allow the extracted formation fluid to bypass the chamber 220. For example, when the valve 224 is closed and the valves 222 and 226 are open, fluid flows from the chamber 218 through the chamber 220 and into the flow-line 230. Fluid may be allowed to flow through the third chamber 220 for a predetermined period of time and/or until a predetermined volume of fluid has passed through the chamber 220 to flush the chamber 220. For example, a volume of fluid equal to or greater than ten times the volume of the chamber 220 may be passed through the chamber 220 prior to making any measurements of the fluid therein using the measurement or analysis capabilities of the chamber 220 described above. However, any other amount of fluid may be used to flush the chamber 220.

Following a flushing of the chamber 220, the valves 222 and 226 may be closed and the valve 224 may be opened. The fluid that bypasses (i.e., flows from the second chamber 218 through the flow line 232 to the flow line 230) the third chamber 220 while the valves 222 and 226 are closed may be passed to a sample collection vessel (not shown). The fluid that remains trapped in the third chamber 220 is subjected to a series of pressure reductions and stabilizations that, in conjunction with the electronics unit 228, enables the detection and identification of the phase transitions of the trapped fluid. In turn, such phase transition information provides additional physical property (e.g., thermophysical property) information associated with the formation fluid. The additional physical property information can then be used to select, adjust and/or tune a mathematical model characterizing the thermophysical properties of the fluid contained in the formation. More specifically, the fluid trapped in the third chamber 220 may be circulated using the recirculation pump (not shown) until the fluid in the chamber 220 is in hydrostatic, thermal, and diffusive equilibria, which may be generally referred to as a steady state condition. Such a steady state condition may be identified by determining that one or more measured parameters (e.g., fluid temperature, pressure, density, etc.) have remained substantially constant (e.g., within a predetermined range) for a plurality of measurement cycles, a predetermined time period, etc. Additionally, because the trapped fluid is in a closed system, there are no chemical reactions occurring and, thus, the trapped fluid maintains a fixed chemical composition.

To detect the phase transitions of the fluid trapped in the chamber 220, the positive displacement pump (not shown) may be used to increase the volume within the chamber 220 (i.e., allow the pressure therein to decrease), the trapped fluid (e.g., a fixed amount of substance) may again be allowed to reach a steady state condition, and various parameters of the trapped fluid may again be measured and recorded via the electronics unit 228. A succession or series of such pressure reduction operations followed by measurements of the fluid in a steady state condition following each pressure reduction can be used by the electronics unit 228 to identify the phase transitions of the formation fluid, which can be used to adjust or tune a thermophysical model of the formation fluid. While the pressure reductions are described above as occurring in a discrete or step-wise manner, the pressure within the third chamber 220 may alternatively be continuously reduced at a constant rate or variable rate and measurements of the fluid can be made at, for example, pre-determined time intervals.

While the example apparatus 200 depicts the tool 202 having three chambers (e.g., the chambers 212, 218, and 220), more, fewer, or no chambers could be used instead. For example, a single chamber could be used to make all needed measurements or, alternatively, all desired measurements could be made directly in one or more flow-lines (e.g., 210, 230, etc.) of the tool 202, thereby eliminating the need to use any chambers.

Figure 13:
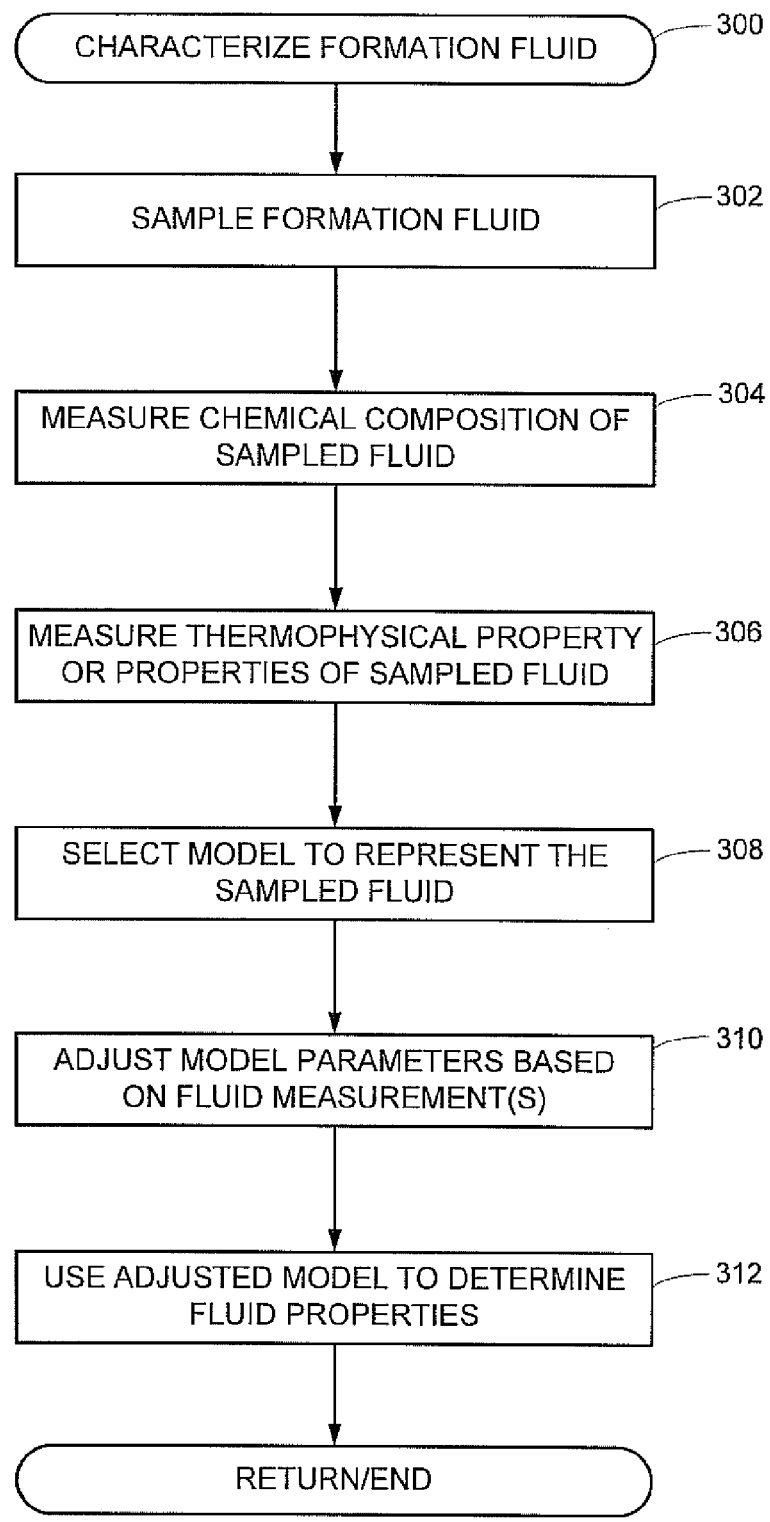
FIG. 13 is a flowchart depicting an example method that may be used in conjunction with the example apparatus of FIG. 12 to characterize a formation fluid.

FIG. 13 is a flowchart depicting an example method 300 that may be used to characterize a formation fluid. Although the example method 300 depicted in FIG. 13 is described as being implemented in connection with the example downhole tool 202 shown in FIG. 12, the method may be implemented using any other suitable downhole tool. Turning in detail to FIG. 13, the method 300 initially samples fluid from the formation 206 (FIG. 12) via the downhole tool 202 (block 302). Specifically, fluid is extracted from the formation 206 via the probe 208 and is passed to the chamber 212 via the flow-line 210.

The sample fluid drawn into the chamber 212 at block 302 is analyzed to determine its chemical composition (block 304). As noted above, the chamber 212 may be configured to employ, for example, optical spectroscopy, gas chromatography, mass spectrometry, and/or nuclear magnetic resonance to determine a chemical composition of the sampled fluid.

The sampled fluid is then passed successively through chambers 218 and 220, within which one or more thermophysical properties of the sampled fluid are measured (block 306). For example, properties such as density, viscosity, heat capacity, thermal conductivity, relative electric permittivity, refractive index, etc. may be measured. Additionally, temperature and pressure (e.g., first temperature and pressure as measure, for example, via the sensors 214 and 216) of the sampled fluid when it is in a single phase (gas, liquid, or solid) may be measured. Still further, thermophysical properties measured by altering the temperature, pressure, and/or chemical composition of the sampled fluid may be obtained. For example, as discussed above in connection with FIG. 12, the pressure within the third chamber 220 may be varied over a range to detect and identify phase transitions or borders such as, (liquid+gas), (liquid+solid), (liquid+liquid+gas), and (liquid +gas+solid). Specifically, asphaltene precipitation can occur when the pressure in the chamber 220 or in the flow-line is reduced. The determination of the onset pressure when the asphaltene starts precipitating can be measured in the chamber 220 when reducing the pressure therein. Alternatively or additionally, in the case where the chamber 220 can be heated and/or cooled independent of the tool 202, the temperature within the chamber 220 can be varied to measure the above-mentioned phase transitions over a range of temperatures. The chemical composition of the sampled fluid may be altered by, for example, injecting a chemical that causes asphaltene precipitation (i.e., a liquid+solid) phase transition.

The example method then selects a mathematical model to represent the sampled fluid (block 308). The selection of a model at block 308 is preferably, but not necessarily, made using chemical composition information obtained at block 304 and/or thermophysical information obtained at block 306. In some examples, the model selected at block 308 may be selected based on another measurement made independently of those made at blocks 304 and 306.

The parameters of the model selected at block 308 are then adjusted based on one or more of the measurements made in connection with blocks 304 and 306 (block 310). Such parameter adjustments may be performed using known techniques. The adjusted model can then be used to estimate or determine properties of the formation fluid at, for example, temperatures and pressures throughout the production system (block 312).

Figure 14A:
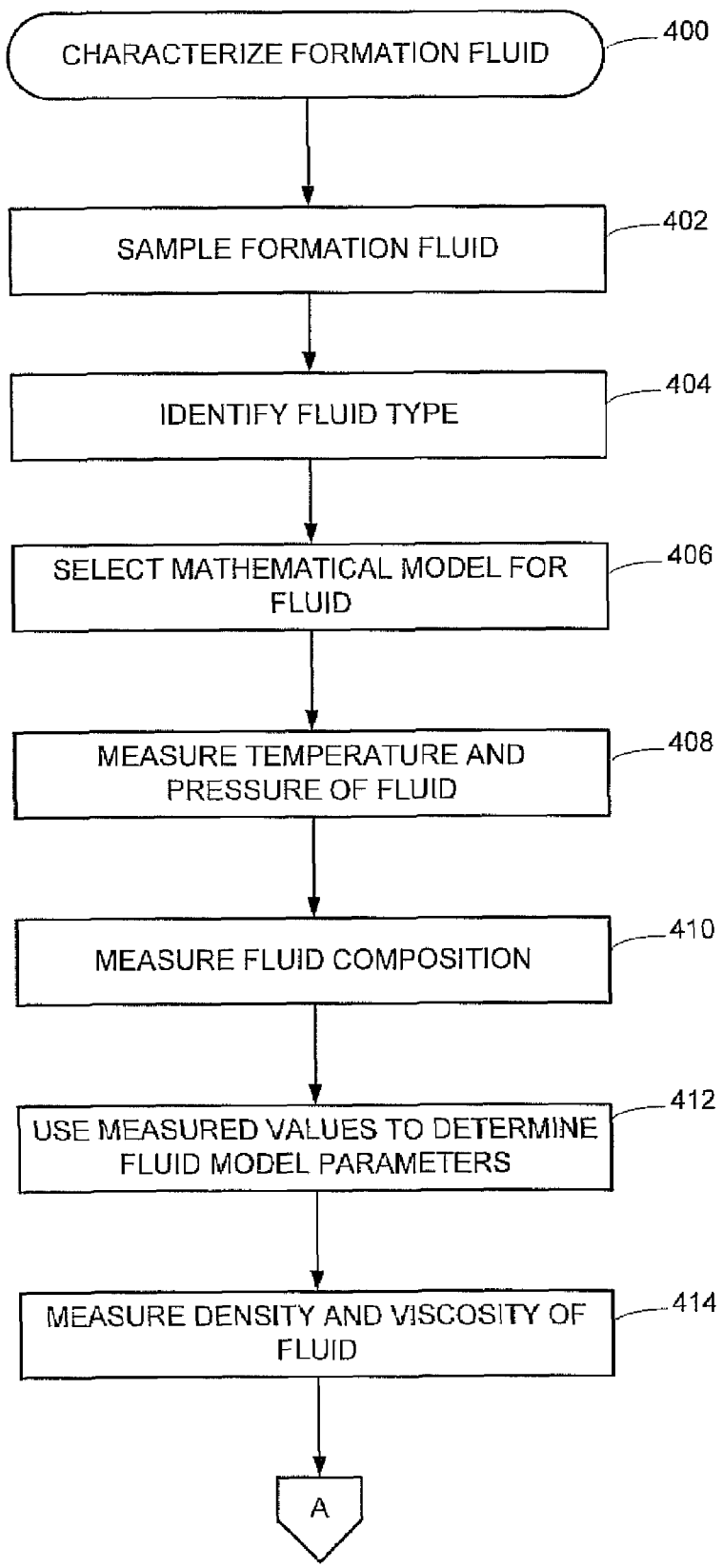
FIGS. 14a and 14b are a flowchart depicting another example method of characterizing a formation fluid.
Figure 14B:
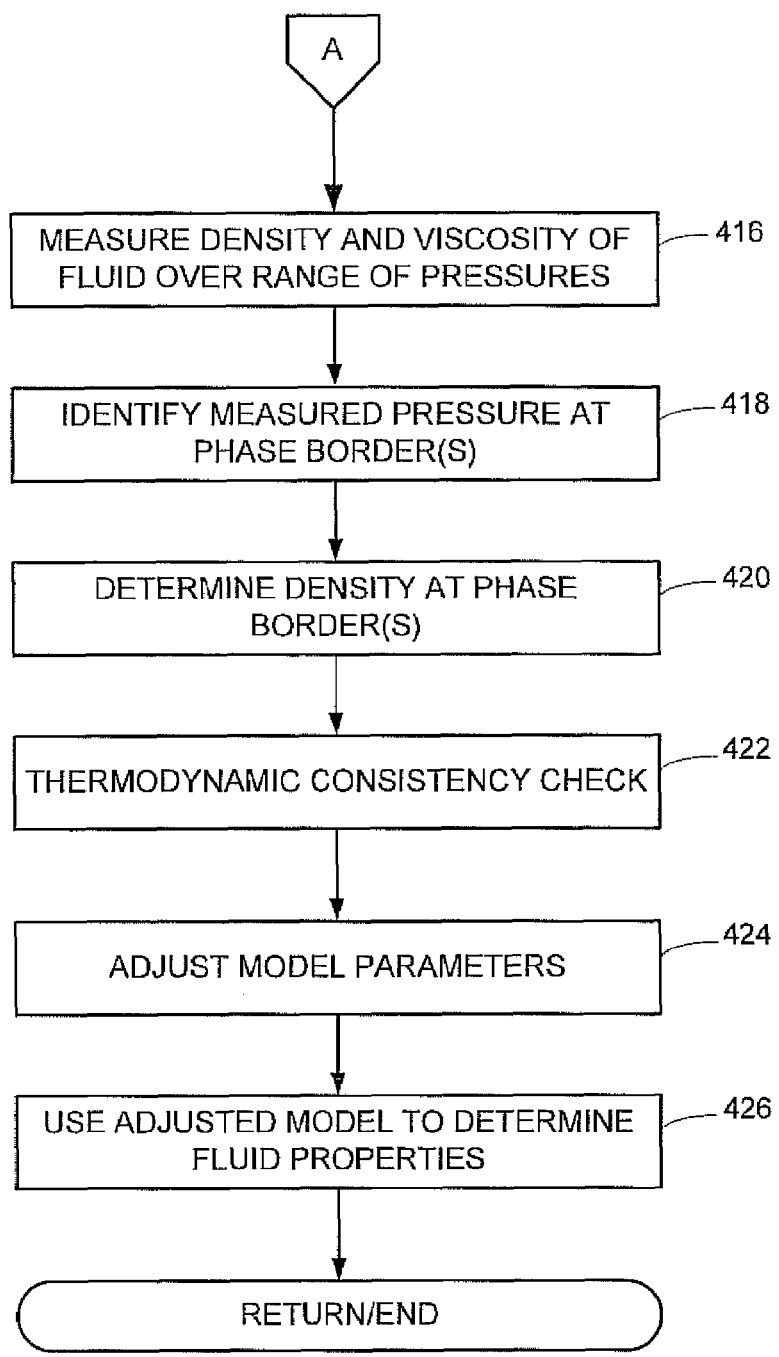

FIGS. 14a and 14b are a flowchart depicting another example method 400 of characterizing a formation fluid. Similar to the foregoing description of the example method 300 of FIG. 13, the example method 400 is described in connection with the example tool 202 of FIG. 12. However, the example method 400 may be more generally implemented using any other suitable tool. Now turning in detail to FIGS. 14a and 14b, the example method 400 samples a formation fluid (block 402) using, for example, the same techniques applied in connection with block 302 of FIG. 13.

The sampled fluid is then analyzed within the chamber 212 to identify the type of the fluid (block 404). As noted above, the fluid type (e.g., oil, gas, water) may be determined using, for example, electric permittivity measurements. The method then selects a mathematical model representing the thermophysical and transport properties of the sampled fluid based on the fluid type (block 406). There are number of known methods by which such models may be selected as well as methods to estimate the chemical composition of sampled fluids. For example, in the case where the sampled fluid is determined to be a gas, one particularly useful thermodynamic model known by the acronym GERG-2004 or EOS NGas can be used to represent the fluid. Another similar model, which does not provide phase behavior information, is known by the acronym AGA8-DC92. Still other known models include Standard-GERG 88, which uses the virial EOS known as MGERG-88 having input parameters of the mole fraction of carbon dioxide, carbon monoxide, nitrogen, hydrogen, hydrocarbon, as well as molar energy content and density. Additional known models include the Goss characterization method (GC92), which uses a combination of CH, N2 and CO2 mole fraction and heat capacity at constant pressure and density, S-GERG, DC92, which was developed by the American Gas Association and combined a virial EOS with an extended Benedict Webb Rubin equation of state, MANGAS, and SUPER-TRAPP. A more detailed description of the various models and composition estimation methods may be found in Danesh, A., "PVT and Phase Behavior of Petroleum Reservoir Fluids, Developments in Petroleum Science," Vol. 47, Elsevier, Amsterdam, 1998, the entire disclosure of which is incorporated herein by reference in its entirety.

The method 400 then measures the temperature and pressure of the sampled fluid using, for example, the sensors 214 and 216. This measured temperature may, for example, correspond to the temperature and pressure of the extracted formation fluid in one or more of the flow-lines 210, 230, and 232. The composition of the fluid is then measured within the chamber 212 using, for example, one or more of the techniques described above in connection with FIG. 13 (block 410). More specifically, at block 410, the chamber 212 may be used to measure the mole fractions of hydrogen sulfide, carbon dioxide, methane, as well as other heavier hydrocarbons.

The method 400 then uses one or more of the measured values obtained at blocks 408 and 410 to determine the appropriate parameter values for the fluid model selected at block 406 (block 412). Such a determination may be made using, for example, continuous thermodynamic techniques, pseudo-component techniques, and/or exponential or gamma probability techniques, etc. The method 400 then measures the density and viscosity of the formation fluid sample at the pressure and temperature measured at block 408 (block 414). The fluid density and viscosity may be measured at block 414 using the second chamber 218 as described above in connection with FIG. 12.

The example method 400 then measures the density and viscosity of the sampled formation fluid over a range of pressures (block 416). Such measurements may be made within the third chamber 220 as described above in connection with FIG. 12. The density and viscosity measurements made at block 416 are then analyzed to identify the measured pressure at the phase transitions or borders (block 418). In particular, the measured pressure at the (liquid+solid) and (liquid+gas) phase borders or boundaries may be identified at block 418. The method 400 then calculates estimated fluid density at the phase borders (e.g., the (liquid+gas) phase border) (block 420). The calculation of the fluid density along the (liquid+gas) phase border may be determined by fitting the measured density values to an empirically derived function where the variable is pressure at tool temperature. This function may then be used to calculate the density at the phase border(s) (e.g., the (liquid+gas) phase border) by extrapolating using the measured phase boundary pressure. Such an extrapolation may be performed by adopting a fixed functional form $\rho(\text{pressure})$ or using a bank of terms and an automated adaptive algorithm where the terms are selected and deselected based on the student -t or F statistic. One such adaptive algorithm is described in Wagner, W. *Cryogenics* 1972, 12, 214-221, which is incorporated by reference herein in its entirety.

The example method 400 then performs a thermodynamic consistency check (block 422). A thermodynamically consistent condition exists when the quantities on both sides of an equality for a thermodynamic relationship (e.g., a mathematical model representing the thermodynamic behavior of a fluid) can be evaluated from measurements to determine that quantities on both sides of the equality do not have to be measured to achieve high confidence results. In this manner, for example, if a fluid model is determined to be thermodynamically consistent, then only values on one side of the equality may need to be measured to make use of the fluid model (e.g., the easier to measure values).

Following the thermodynamic consistency check at block 422, the example method 400 may adjust the model parameters (block 424) and then use the adjusted model to determine fluid properties (block 426). The fluid properties determined at block 426 may be associated with, for example, temperatures and/or pressures experienced throughout the production process.

There have been described and illustrated herein examples of methods and apparatus for characterizing formation fluids. While particular examples have been described, it is not intended that the invention be limited thereto, as it is intended that the invention be as broad in scope as the art will allow and that the specification be read likewise. Thus, while the examples are described with reference to generating P-T diagrams, it will be appreciated that the actual diagrams need not get generated, and that useful determinations can be made by finding specific points of interest such as the critical point and/or the bubble point or dew point for a particular in situ temperature. Further, while certain particular tools and modules such as the MDT and CGA were described, it will be appreciated that other tools capable of making determinations of fluid constituents may be utilized. It will therefore be appreciated by those skilled in the art that yet other modifications could be made to the provided invention without deviating from its spirit and scope as claimed.

Thus, while certain example apparatus and methods have been described herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. A method to characterize a fluid associated with an underground geological formation, comprising:
   obtaining a sample of the fluid associated with the underground geological formation;
   measuring, in a borehole associated with the underground geological formation, a chemical composition of the sample of the fluid;
   measuring, in the borehole, a thermophysical property of the sample of the fluid;
   selecting a mathematical model to represent the sample of the fluid based on at least one of the chemical composition or the thermophysical property;
   adjusting a parameter of the mathematical model based on at least one of the chemical composition or the thermophysical property to generate an adjusted mathematical model; and
   determining a property of the fluid associated with the underground geological formation based on the adjusted mathematical model.

2. The method as defined in claim 1, wherein measuring the chemical composition of the sample of the fluid comprises measuring mole fraction or mass fraction constituents of the sample of the fluid.

3. The method as defined in claim 1, wherein measuring the thermophysical property of the sample of the fluid comprises measuring at least one of a density, a viscosity, a heat capacity, a thermal conductivity, a relative electric permittivity, or a refractive index of the sample of the fluid.

4. A method as defined in claim 1, wherein measuring the thermophysical property of the sample of the fluid comprises measuring the thermophysical property over at least one of a range of temperatures or pressures to generate a range of thermophysical property values.

5. The method as defined in claim 4, further comprising detecting at least one of a phase transition or phase border of the sample of the fluid during the generation of the range of thermophysical property values.

6. The method as defined in claim 1, wherein measuring the thermophysical property of the sample of the fluid comprises determining an amount of a chemical added to the sample of the fluid that causes a phase transition of the sample of the fluid.

7. The method as defined in claim 1, wherein selecting the mathematical model comprises selecting the mathematical model based on at least one of identifying a type of the sample of the fluid or a chemical composition of the sample of the fluid.

8. The method as defined in claim 1, wherein determining the property of the fluid associated with the underground geological formation based on the adjusted mathematical model comprises determining the property of the fluid associated with the underground geological formation at a temperature or a pressure associated with producing fluid from the underground geological formation.

9. The method as defined in claim 1, further comprising performing a thermodynamic consistency check prior to adjusting the parameter of the mathematical model.

10. A system to characterize a fluid associated with an underground geological formation, comprising:
a device to obtain a sample of the fluid associated with the underground geological formation;
a first sensor to measure a chemical composition of the sample of the fluid;
a second sensor to measure a thermophysical property of the sample of the fluid; and
an electronics unit to select a mathematical model to represent the sample of the fluid based on at least one of the chemical composition or the thermophysical property, wherein the electronics unit is to adjust a parameter of the mathematical model based on at least one of the chemical composition or the thermophysical property to generate an adjusted mathematical model, and wherein the electronics unit is to determine a property of the fluid associated with the underground geological formation based on the adjusted mathematical model.

11. The system as defined in claim 10, wherein the device comprises at least one of a probe or a dual packer.

12. The system as defined in claim 10, further comprising a chamber to vary at least a pressure or a temperature of the sample of the fluid.

13. The system as defined in claim 12, wherein the electronics unit is to detect at least one of a phase transition or phase border of the sample of the fluid during the varying of the at least the pressure or the temperature of the sample of the fluid.

14. The system as defined in claim 12, further comprising a plurality of valves to selectively trap fluid within the chamber.

15. The system as defined in claim 12, wherein the chamber is to add an amount of a chemical to the sample of the fluid that causes a phase transition of the sample of the fluid.

16. The system as defined in claim 10, further comprising at least one of a temperature sensor or a pressure sensor to measure a temperature or a pressure of the sample of the fluid in a flow-line.

17. The system as defined in claim 10, wherein the electronics unit is to select the mathematical model based on at least one of identifying a type of the sample of the fluid or a chemical composition of the sample of the fluid.

18. The system as defined in claim 10, wherein the electronics unit is to determine the property of the fluid associated with the underground geological formation based on the adjusted mathematical model by determining the property of the fluid associated with the underground geological formation at a temperature or a pressure associated with producing fluid from the underground geological formation.

19. The system as defined in claim 10, wherein the electronics unit is to perform a thermodynamic consistency check prior to adjusting the parameter of the mathematical model.

20. The system of claim 10, wherein the device is configured to be deployed within a borehole that penetrates the geological formation via wire-line or drill pipe.

* * * * *